United States Patent
Carey et al.

(10) Patent No.: US 11,737,845 B2
(45) Date of Patent: Aug. 29, 2023

(54) MEDICAL INSTRUMENT WITH A CAPSTAN

(71) Applicant: Auris Health, Inc., Redwood City, CA (US)

(72) Inventors: Dillon Robert Carey, Belmont, CA (US); Aren Calder Hill, Mountain View, CA (US)

(73) Assignee: Auris Inc., Redwood City, CA (US)

( * ) Notice: Subject to any disclaimer, the term of this patent is extended or adjusted under 35 U.S.C. 154(b) by 309 days.

(21) Appl. No.: 17/033,154

(22) Filed: Sep. 25, 2020

(65) Prior Publication Data

US 2021/0093408 A1    Apr. 1, 2021

Related U.S. Application Data

(60) Provisional application No. 62/908,446, filed on Sep. 30, 2019.

(51) Int. Cl.
*A61B 34/00* (2016.01)
*A61B 90/50* (2016.01)
*A61B 34/37* (2016.01)
*A61B 34/30* (2016.01)

(52) U.S. Cl.
CPC .............. *A61B 34/71* (2016.02); *A61B 34/37* (2016.02); *A61B 90/50* (2016.02); *A61B 2034/301* (2016.02)

(58) Field of Classification Search
CPC ......... A61B 34/71; A61B 34/37; A61B 90/50; A61B 2034/301; A61B 2017/00477; A61B 34/30; A61B 2034/715
USPC ........................................................ 606/130
See application file for complete search history.

(56) References Cited

U.S. PATENT DOCUMENTS

| | | | |
|---|---|---|---|
| 2,556,601 | A | 6/1951 | Schofield |
| 2,566,183 | A | 8/1951 | Forss |
| 2,623,175 | A | 12/1952 | Finke |
| 2,730,699 | A | 1/1956 | Gratian |
| 2,884,808 | A | 5/1959 | Mueller |
| 3,294,183 | A | 12/1966 | Riley et al. |
| 3,472,083 | A | 10/1969 | Schnepel |

(Continued)

FOREIGN PATENT DOCUMENTS

| | | |
|---|---|---|
| CN | 101161426 | 4/2008 |
| CN | 101443069 | 5/2009 |

(Continued)

OTHER PUBLICATIONS

Ramezanifard et al, 2007, A Novel Modeling Approach for Collision Avoidance in Robotic Surgery, 2007 Science Publications, American Journal of Applied Sciences 4(9):693-699.

(Continued)

*Primary Examiner* — Tan-Uyen T Ho
*Assistant Examiner* — Regina Vahey
(74) *Attorney, Agent, or Firm* — Frost Brown Todd LLP

(57) ABSTRACT

Certain aspects relate to systems and techniques for robotic medical instrument system. The medical instrument system can include a pulley and a capstan. The capstan can be supported for rotation about a rotational axis and translation along the rotational axis. A cable can be wrapped around the capstan and extending from the capstan to the pulley. The capstan can be configured to translate relative to the pulley along the rotational axis as the capstan rotates about the rotational axis.

23 Claims, 25 Drawing Sheets

(56) References Cited

U.S. PATENT DOCUMENTS

| | | |
|---|---|---|
| 3,513,724 A | 5/1970 | Box |
| 3,595,074 A | 7/1971 | Johnson |
| 3,734,207 A | 5/1973 | Fishbein |
| 3,739,923 A | 6/1973 | Totsuka |
| 3,763,860 A | 10/1973 | Clarke |
| 3,784,031 A | 1/1974 | Nitu |
| 3,790,002 A | 2/1974 | Guilbaud et al. |
| 3,921,536 A | 11/1975 | Savage |
| 3,926,386 A | 12/1975 | Stahmann |
| 4,040,413 A | 8/1977 | Ohshiro |
| 4,141,245 A | 2/1979 | Brandstetter |
| 4,198,960 A | 4/1980 | Utsugi |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,470,407 A | 9/1984 | Hussein |
| 4,507,026 A | 3/1985 | Lund |
| 4,530,471 A | 7/1985 | Inoue |
| 4,532,935 A | 8/1985 | Wang et al. |
| 4,555,960 A | 12/1985 | King |
| 4,685,458 A | 8/1987 | Leckrone |
| 4,688,555 A | 8/1987 | Wardle |
| 4,745,908 A | 5/1988 | Wardle |
| 4,747,405 A | 5/1988 | Leckrone |
| 4,784,150 A | 11/1988 | Voorhies et al. |
| 4,854,301 A | 8/1989 | Nakajima |
| 4,857,058 A | 8/1989 | Payton |
| 4,898,574 A | 2/1990 | Uchiyama et al. |
| 4,907,168 A | 3/1990 | Boggs |
| 4,945,790 A | 8/1990 | Golden |
| 4,983,165 A | 1/1991 | Loiterman |
| 5,029,574 A | 7/1991 | Shimamura et al. |
| 5,085,659 A | 2/1992 | Rydell |
| 5,150,452 A | 9/1992 | Pollack et al. |
| 5,196,023 A | 3/1993 | Martin |
| 5,207,128 A | 5/1993 | Albright |
| 5,217,465 A | 6/1993 | Steppe |
| 5,234,428 A | 8/1993 | Kaufman |
| 5,256,150 A | 10/1993 | Quiachon et al. |
| 5,277,085 A | 1/1994 | Tanimura et al. |
| 5,308,323 A | 5/1994 | Sogawa et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,350,101 A | 9/1994 | Godlewski |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume |
| 5,426,687 A | 6/1995 | Goodall et al. |
| 5,431,649 A | 7/1995 | Mulier et al. |
| 5,441,485 A | 8/1995 | Peters |
| 5,449,356 A | 9/1995 | Walbrink |
| 5,450,843 A | 9/1995 | Moll et al. |
| 5,472,426 A | 12/1995 | Bonati et al. |
| 5,496,267 A | 3/1996 | Drasler |
| 5,501,667 A | 3/1996 | Verduin, Jr. |
| 5,507,725 A | 4/1996 | Savage et al. |
| 5,520,684 A | 5/1996 | Imran |
| 5,524,180 A | 6/1996 | Wang et al. |
| 5,545,170 A | 8/1996 | Hart |
| 5,559,294 A | 9/1996 | Hoium et al. |
| 5,562,239 A | 10/1996 | Boiarski et al. |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,695,500 A | 12/1997 | Taylor et al. |
| 5,697,949 A | 12/1997 | Giurtino et al. |
| 5,709,661 A | 1/1998 | Van Egmond |
| 5,710,870 A | 1/1998 | Ohm |
| 5,716,325 A | 2/1998 | Bonutti |
| 5,737,500 A | 4/1998 | Seraji et al. |
| 5,767,840 A | 6/1998 | Selker |
| 5,779,623 A | 7/1998 | Bonnell |
| 5,788,667 A | 8/1998 | Stoller |
| 5,792,135 A | 8/1998 | Madhani et al. |
| 5,792,165 A | 8/1998 | Klieman |
| 5,797,900 A | 8/1998 | Madhani |
| 5,798,627 A | 8/1998 | Gilliland |
| 5,810,770 A | 9/1998 | Chin et al. |
| 5,842,390 A | 12/1998 | Bouligny |
| 5,855,583 A | 1/1999 | Wang et al. |
| 5,893,869 A | 4/1999 | Barhart |
| 5,897,491 A | 4/1999 | Kastenbauer et al. |
| 5,921,968 A | 7/1999 | Lampropoulos et al. |
| 5,924,175 A | 7/1999 | Lippitt |
| 5,943,056 A | 8/1999 | Sato |
| 5,967,934 A | 10/1999 | Ishida et al. |
| 5,989,230 A | 11/1999 | Frassica |
| 6,071,281 A | 6/2000 | Burnside et al. |
| 6,077,219 A | 6/2000 | Viebach |
| 6,084,371 A | 7/2000 | Kress et al. |
| 6,093,157 A | 7/2000 | Chandrasekaran |
| 6,110,171 A | 8/2000 | Rydell |
| 6,120,476 A | 9/2000 | Fung et al. |
| 6,120,498 A | 9/2000 | Jani et al. |
| 6,154,000 A | 11/2000 | Rastegar et al. |
| 6,156,030 A | 12/2000 | Neev |
| 6,171,234 B1 | 1/2001 | White et al. |
| 6,174,318 B1 | 1/2001 | Bates et al. |
| 6,183,435 B1 | 2/2001 | Bumbalough et al. |
| 6,185,478 B1 | 2/2001 | Koakutsu et al. |
| 6,206,903 B1 | 3/2001 | Ramans |
| 6,236,906 B1 | 5/2001 | Muller |
| 6,272,371 B1 | 8/2001 | Shlomo |
| 6,289,579 B1 | 9/2001 | Viza et al. |
| 6,322,557 B1 | 11/2001 | Nikolaevich |
| 6,375,635 B1 | 4/2002 | Moutafis |
| 6,394,998 B1 | 5/2002 | Wallace et al. |
| 6,401,572 B1 | 6/2002 | Provost |
| 6,405,078 B1 | 6/2002 | Moaddeb et al. |
| 6,436,107 B1 | 8/2002 | Wang et al. |
| 6,440,061 B1 | 8/2002 | Wenner et al. |
| 6,487,940 B2 | 12/2002 | Hart et al. |
| 6,491,701 B2 | 12/2002 | Tierney et al. |
| 6,508,823 B1 | 1/2003 | Gonon |
| 6,522,906 B1 | 2/2003 | Salisbury et al. |
| 6,577,891 B1 | 6/2003 | Jaross et al. |
| 6,676,668 B2 | 1/2004 | Mercereau et al. |
| 6,685,698 B2 | 2/2004 | Morley et al. |
| 6,695,818 B2 | 2/2004 | Wollschlager |
| 6,706,050 B1 | 3/2004 | Giannadakis |
| 6,726,675 B1 | 4/2004 | Beyar |
| 6,786,896 B1 | 9/2004 | Madhani et al. |
| 6,827,712 B2 | 12/2004 | Tovey et al. |
| 7,044,936 B2 | 5/2006 | Harding |
| 7,172,580 B2 | 2/2007 | Hruska et al. |
| 7,248,944 B2 | 7/2007 | Green |
| 7,276,044 B2 | 10/2007 | Ferry et al. |
| 7,282,055 B2 | 10/2007 | Tsuruta |
| 7,559,934 B2 | 7/2009 | Teague et al. |
| 7,615,042 B2 | 11/2009 | Beyar et al. |
| 7,635,342 B2 | 12/2009 | Ferry et al. |
| 7,736,356 B2 | 6/2010 | Cooper et al. |
| 7,766,856 B2 | 8/2010 | Ferry et al. |
| 7,882,841 B2 | 2/2011 | Aljuri |
| 7,938,809 B2 | 5/2011 | Lampropoulos et al. |
| 7,963,911 B2 | 6/2011 | Turliuc |
| 7,972,298 B2 | 7/2011 | Wallace et al. |
| 7,974,674 B2 | 7/2011 | Hauck et al. |
| 7,987,046 B1 | 7/2011 | Peterman |
| 7,998,020 B2 | 8/2011 | Kidd et al. |
| 8,002,713 B2 | 8/2011 | Heske |
| 8,004,229 B2 | 8/2011 | Nowlin et al. |
| 8,038,598 B2 | 10/2011 | Khachi |
| 8,052,636 B2 | 11/2011 | Moll et al. |

(56) References Cited

U.S. PATENT DOCUMENTS

| | | |
|---|---|---|
| 8,092,397 B2 | 1/2012 | Wallace et al. |
| 8,157,308 B2 | 4/2012 | Pedersen |
| 8,182,415 B2 | 5/2012 | Larkin et al. |
| 8,187,173 B2 | 5/2012 | Miyoshi |
| 8,257,303 B2 | 9/2012 | Moll et al. |
| 8,277,417 B2 | 10/2012 | Fedinec et al. |
| 8,291,791 B2 | 10/2012 | Light et al. |
| 8,414,505 B1 | 4/2013 | Weitzner |
| 8,425,465 B2 | 4/2013 | Nagano |
| 8,480,595 B2 | 7/2013 | Speeg |
| 8,523,762 B2 | 9/2013 | Miyamoto et al. |
| 8,540,748 B2 | 9/2013 | Murphy et al. |
| 8,541,970 B2 | 9/2013 | Nowlin |
| 8,671,817 B1 | 3/2014 | Bogusky |
| 8,720,448 B2 | 5/2014 | Reis et al. |
| 8,746,252 B2 | 6/2014 | McGrogan et al. |
| 8,749,190 B2 | 6/2014 | Nowlin et al. |
| 8,786,241 B2 | 7/2014 | Nowlin et al. |
| 8,820,603 B2 | 9/2014 | Shelton et al. |
| 8,821,480 B2 | 9/2014 | Burbank |
| 8,870,815 B2 | 10/2014 | Bhat et al. |
| 8,882,660 B2 | 11/2014 | Phee et al. |
| 8,945,163 B2 | 2/2015 | Voegele et al. |
| 8,956,280 B2 | 2/2015 | Eversull et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,173,713 B2 | 11/2015 | Hart et al. |
| 9,179,979 B2 | 11/2015 | Jinno |
| 9,204,933 B2 | 12/2015 | Reis et al. |
| 9,259,280 B2 | 2/2016 | Au |
| 9,259,281 B2 | 2/2016 | Griffiths et al. |
| 9,259,282 B2 | 2/2016 | Azizian |
| 9,296,104 B2 | 3/2016 | Swarup et al. |
| 9,326,822 B2 | 5/2016 | Lewis et al. |
| 9,345,456 B2 | 5/2016 | Tsonton et al. |
| 9,345,544 B2 | 5/2016 | Hourtash et al. |
| 9,375,284 B2 | 6/2016 | Hourtash |
| 9,408,669 B2 | 8/2016 | Kokish et al. |
| 9,415,510 B2 | 8/2016 | Hourtash et al. |
| 9,446,177 B2 | 9/2016 | Millman et al. |
| 9,452,018 B2 | 9/2016 | Yu |
| 9,457,168 B2 | 10/2016 | Moll et al. |
| 9,460,536 B2 | 10/2016 | Hasegawa et al. |
| 9,480,534 B2 | 11/2016 | Bowling |
| 9,498,601 B2 | 11/2016 | Tanner et al. |
| 9,504,604 B2 | 11/2016 | Alvarez |
| 9,510,911 B2 | 12/2016 | Hourtash |
| 9,517,106 B2 | 12/2016 | Hourtash et al. |
| 9,561,083 B2 | 2/2017 | Yu et al. |
| 9,566,125 B2 | 2/2017 | Bowling |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,675,422 B2 | 6/2017 | Hourtash et al. |
| 9,687,310 B2 | 6/2017 | Nowlin et al. |
| 9,713,509 B2 | 7/2017 | Schuh et al. |
| 9,727,963 B2 | 8/2017 | Mintz et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,943,962 B2 | 4/2018 | Sattler et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,993,614 B2 | 6/2018 | Pacheco |
| 10,016,900 B1 | 7/2018 | Meyer et al. |
| 10,022,192 B1 | 7/2018 | Ummalaneni |
| 10,029,367 B2 | 7/2018 | Hourtash |
| 10,046,140 B2 | 8/2018 | Kokish et al. |
| 10,071,479 B2 | 9/2018 | Swarup et al. |
| 10,080,576 B2 | 9/2018 | Romo et al. |
| 10,117,713 B2 | 11/2018 | Moctezuma de la Barrera |
| 10,130,429 B1 | 11/2018 | Weir |
| 10,136,949 B2 | 11/2018 | Felder et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,154,822 B2 | 12/2018 | Henderson |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,868 B2 | 3/2019 | Weir |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,258,285 B2 | 4/2019 | Hauck |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,314,661 B2 | 6/2019 | Bowling |
| 10,327,855 B2 | 6/2019 | Hourtash et al. |
| 10,350,017 B2 | 7/2019 | Bowling |
| 10,350,390 B2 | 7/2019 | Moll et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,454,347 B2 | 10/2019 | Covington et al. |
| 10,463,440 B2 | 11/2019 | Bowling |
| 10,464,209 B2 | 11/2019 | Ho et al. |
| 10,470,830 B2 | 11/2019 | Hill |
| 10,478,595 B2 | 11/2019 | Kokish |
| 10,482,599 B2 | 11/2019 | Mintz et al. |
| 10,493,239 B2 | 12/2019 | Hart et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,524,867 B2 | 1/2020 | Kokish et al. |
| 10,539,478 B2 | 1/2020 | Lin |
| 10,543,047 B2 | 1/2020 | Yu |
| 10,543,048 B2 | 1/2020 | Noonan et al. |
| 10,555,778 B2 | 2/2020 | Ummalaneni et al. |
| 10,556,092 B2 | 2/2020 | Yu et al. |
| 10,569,052 B2 | 2/2020 | Kokish et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,667,875 B2 | 6/2020 | DeFonzo |
| 10,682,189 B2 | 6/2020 | Schuh et al. |
| 10,687,903 B2 | 6/2020 | Lewis et al. |
| 10,695,536 B2 | 6/2020 | Weitzner et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,779,898 B2 | 9/2020 | Hill |
| 10,786,329 B2 | 9/2020 | Schuh et al. |
| 10,786,432 B2 | 9/2020 | Jornitz et al. |

(56) References Cited

U.S. PATENT DOCUMENTS

| | | |
|---|---|---|
| 10,792,112 B2 | 10/2020 | Kokish et al. |
| 10,792,464 B2 | 10/2020 | Romo et al. |
| 10,792,466 B2 | 10/2020 | Landey et al. |
| 10,813,539 B2 | 10/2020 | Graetzel et al. |
| 10,814,101 B2 | 10/2020 | Jiang |
| 10,820,947 B2 | 11/2020 | Julian |
| 10,820,952 B2 | 11/2020 | Yu |
| 10,820,954 B2 | 11/2020 | Marsot et al. |
| 10,827,913 B2 | 11/2020 | Ummalaneni et al. |
| 10,828,118 B2 | 11/2020 | Schuh et al. |
| 10,835,153 B2 | 11/2020 | Rafii-Tari et al. |
| 10,850,013 B2 | 12/2020 | Hsu |
| 10,881,280 B2 | 1/2021 | Baez |
| 2001/0042643 A1 | 11/2001 | Krueger et al. |
| 2002/0019644 A1 | 2/2002 | Hastings |
| 2002/0045905 A1 | 4/2002 | Gerbi et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0111608 A1 | 8/2002 | Baerveldt |
| 2002/0111621 A1 | 8/2002 | Wallace et al. |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0004455 A1 | 1/2003 | Kadziauskas |
| 2003/0040681 A1 | 2/2003 | Ng et al. |
| 2003/0056561 A1 | 3/2003 | Butscher et al. |
| 2003/0065358 A1 | 4/2003 | Frecker |
| 2003/0100892 A1 | 5/2003 | Morley et al. |
| 2003/0109780 A1 | 6/2003 | Coste-Maniere et al. |
| 2003/0109877 A1 | 6/2003 | Morley |
| 2003/0109889 A1 | 6/2003 | Mercereau |
| 2003/0158545 A1 | 8/2003 | Hovda et al. |
| 2003/0167623 A1 | 9/2003 | Lorenz |
| 2003/0208189 A1 | 11/2003 | Payman |
| 2003/0212308 A1 | 11/2003 | Bendall |
| 2004/0015053 A1 | 1/2004 | Bieger |
| 2004/0143253 A1 | 7/2004 | Vanney |
| 2004/0152972 A1 | 8/2004 | Hunter |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee et al. |
| 2004/0210116 A1 | 10/2004 | Nakao |
| 2004/0243147 A1 | 12/2004 | Lipow |
| 2004/0253079 A1 | 12/2004 | Sanchez |
| 2004/0254566 A1 | 12/2004 | Plicchi |
| 2005/0004579 A1 | 1/2005 | Schneider et al. |
| 2005/0033270 A1 | 2/2005 | Ramans et al. |
| 2005/0054900 A1 | 3/2005 | Mawn |
| 2005/0159645 A1 | 7/2005 | Bertolero |
| 2005/0177026 A1 | 8/2005 | Hoeg et al. |
| 2005/0183532 A1 | 8/2005 | Najaf et al. |
| 2005/0222554 A1 | 10/2005 | Wallace et al. |
| 2005/0240178 A1 | 10/2005 | Morley et al. |
| 2005/0261705 A1 | 11/2005 | Gist |
| 2006/0015133 A1 | 1/2006 | Grayzel |
| 2006/0041245 A1 | 2/2006 | Ferry |
| 2006/0058813 A1 | 3/2006 | Teague |
| 2006/0111692 A1 | 5/2006 | Hlavka et al. |
| 2006/0116693 A1 | 6/2006 | Weisenburgh |
| 2006/0135963 A1 | 6/2006 | Kick |
| 2006/0142657 A1 | 6/2006 | Quaid |
| 2006/0146010 A1 | 7/2006 | Schneider |
| 2006/0156875 A1 | 7/2006 | McRury et al. |
| 2006/0161137 A1 | 7/2006 | Orban et al. |
| 2006/0189891 A1 | 8/2006 | Waxman et al. |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0060879 A1 | 3/2007 | Weitzner et al. |
| 2007/0100201 A1 | 5/2007 | Komiya et al. |
| 2007/0100254 A1 | 5/2007 | Murakami |
| 2007/0106304 A1 | 5/2007 | Hammack |
| 2007/0112355 A1 | 5/2007 | Salahieh |
| 2007/0119274 A1 | 5/2007 | Devengenzo et al. |
| 2007/0123355 A1 | 5/2007 | Morley et al. |
| 2007/0135803 A1 | 6/2007 | Belson |
| 2007/0149946 A1 | 6/2007 | Viswanathan |
| 2007/0185485 A1 | 8/2007 | Hauck et al. |
| 2007/0191177 A1 | 8/2007 | Nagai et al. |
| 2007/0208375 A1 | 9/2007 | Nishizawa |
| 2007/0213668 A1 | 9/2007 | Spitz |
| 2007/0239028 A1 | 10/2007 | Houser |
| 2007/0239178 A1 | 10/2007 | Weitzner et al. |
| 2007/0245175 A1 | 10/2007 | Zheng et al. |
| 2007/0250111 A1 | 10/2007 | Lu |
| 2007/0299427 A1 | 12/2007 | Yeung et al. |
| 2008/0009838 A1* | 1/2008 | Schena ................. A61B 34/71 606/1 |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0039255 A1 | 2/2008 | Jinno et al. |
| 2008/0045981 A1 | 2/2008 | Margolin et al. |
| 2008/0046122 A1 | 2/2008 | Manzo et al. |
| 2008/0065103 A1 | 3/2008 | Cooper et al. |
| 2008/0065111 A1 | 3/2008 | Blumenkranz |
| 2008/0065112 A1 | 3/2008 | Tovey et al. |
| 2008/0125698 A1 | 5/2008 | Greg et al. |
| 2008/0147011 A1 | 6/2008 | Urmey |
| 2008/0177285 A1 | 7/2008 | Brock et al. |
| 2008/0187101 A1 | 8/2008 | Gertner |
| 2008/0196533 A1 | 8/2008 | Bergamasco |
| 2008/0214925 A1 | 9/2008 | Wilson et al. |
| 2008/0228104 A1 | 9/2008 | Uber et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0287963 A1 | 11/2008 | Rogers et al. |
| 2008/0302200 A1 | 12/2008 | Tobey |
| 2009/0005768 A1 | 1/2009 | Sharareh |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck |
| 2009/0082634 A1 | 3/2009 | Kathrani et al. |
| 2009/0082722 A1 | 3/2009 | Munger et al. |
| 2009/0088774 A1 | 4/2009 | Swarup et al. |
| 2009/0098971 A1 | 4/2009 | Ho et al. |
| 2009/0105645 A1 | 4/2009 | Kidd et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0163948 A1 | 6/2009 | Sunaoshi |
| 2009/0171371 A1 | 7/2009 | Nixon |
| 2009/0192524 A1 | 7/2009 | Ltkowitz |
| 2009/0227998 A1 | 9/2009 | Aljuri |
| 2009/0247944 A1 | 10/2009 | Kirschenman et al. |
| 2009/0248039 A1 | 10/2009 | Cooper et al. |
| 2009/0248041 A1 | 10/2009 | Williams et al. |
| 2009/0248043 A1 | 10/2009 | Tiemey et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2009/0312773 A1 | 12/2009 | Cabrera et al. |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0016852 A1 | 1/2010 | Manzo et al. |
| 2010/0016853 A1 | 1/2010 | Burbank |
| 2010/0030023 A1 | 2/2010 | Yoshie |
| 2010/0069833 A1 | 3/2010 | Wenderow et al. |
| 2010/0073150 A1 | 3/2010 | Olson et al. |

(56) References Cited

U.S. PATENT DOCUMENTS

| | | |
|---|---|---|
| 2010/0081965 A1 | 4/2010 | Mugan et al. |
| 2010/0082017 A1 | 4/2010 | Zickler |
| 2010/0082041 A1 | 4/2010 | Prisco |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0210923 A1 | 8/2010 | Li et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0248177 A1 | 9/2010 | Mangelberger et al. |
| 2010/0249506 A1 | 9/2010 | Prisco et al. |
| 2010/0268211 A1 | 10/2010 | Manwaring et al. |
| 2010/0274078 A1 | 10/2010 | Kim et al. |
| 2010/0312141 A1 | 12/2010 | Keast et al. |
| 2010/0331858 A1 | 12/2010 | Simaan et al. |
| 2010/0332033 A1 | 12/2010 | Diolaiti |
| 2011/0009863 A1 | 1/2011 | Stanislaw |
| 2011/0015483 A1 | 1/2011 | Barbagli |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028790 A1 | 2/2011 | Farr et al. |
| 2011/0028991 A1 | 2/2011 | Ikeda et al. |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0160713 A1 | 6/2011 | Neuberger |
| 2011/0160745 A1 | 6/2011 | Fielding |
| 2011/0167611 A1 | 7/2011 | Williams |
| 2011/0184391 A1 | 7/2011 | Aljuri |
| 2011/0208211 A1 | 8/2011 | Whitfield et al. |
| 2011/0213362 A1 | 9/2011 | Cunningham |
| 2011/0224660 A1 | 9/2011 | Neuberger et al. |
| 2011/0238064 A1 | 9/2011 | Williams et al. |
| 2011/0238083 A1 | 9/2011 | Moll et al. |
| 2011/0257641 A1 | 10/2011 | Hastings et al. |
| 2011/0261183 A1 | 10/2011 | Ma et al. |
| 2011/0276085 A1 | 11/2011 | Krzyzanowski |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2011/0313343 A1 | 12/2011 | Milutinovic et al. |
| 2012/0048759 A1 | 3/2012 | Disch et al. |
| 2012/0069167 A1 | 3/2012 | Liu et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0132018 A1 | 5/2012 | Tang |
| 2012/0136419 A1 | 5/2012 | Zarembo et al. |
| 2012/0138586 A1 | 6/2012 | Webster et al. |
| 2012/0138660 A1 | 6/2012 | Shelton, IV et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0209315 A1 | 8/2012 | Amat |
| 2012/0217457 A1 | 8/2012 | Schena et al. |
| 2012/0232342 A1 | 9/2012 | Reydel |
| 2012/0232476 A1 | 9/2012 | Bhat et al. |
| 2012/0239012 A1 | 9/2012 | Laurent et al. |
| 2012/0253277 A1 | 10/2012 | Tah et al. |
| 2012/0253332 A1 | 10/2012 | Moll |
| 2012/0259320 A1 | 10/2012 | Loesel et al. |
| 2012/0277730 A1 | 11/2012 | Salahieh |
| 2012/0283747 A1 | 11/2012 | Popovic |
| 2012/0296318 A1 | 11/2012 | Wellhofer et al. |
| 2013/0006144 A1 | 1/2013 | Clancy |
| 2013/0018400 A1 | 1/2013 | Milton et al. |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0066335 A1 | 3/2013 | Barwinkel |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith |
| 2013/0116716 A1 | 5/2013 | Bahls et al. |
| 2013/0144116 A1 | 6/2013 | Cooper et al. |
| 2013/0144274 A1 | 6/2013 | Stefanchik et al. |
| 2013/0144395 A1 | 6/2013 | Stefanchik |
| 2013/0190796 A1 | 7/2013 | Tilson et al. |
| 2013/0204124 A1 | 8/2013 | Duindam |
| 2013/0225997 A1 | 8/2013 | Dillard et al. |
| 2013/0226151 A1 | 8/2013 | Suehara |
| 2013/0226161 A1 | 8/2013 | Hickenbotham |
| 2013/0231678 A1 | 9/2013 | Wenderow |
| 2013/0233908 A1 | 9/2013 | Knodel |
| 2013/0253267 A1 | 9/2013 | Collins |
| 2013/0303876 A1 | 11/2013 | Gelfand et al. |
| 2013/0304084 A1 | 11/2013 | Beira et al. |
| 2013/0310819 A1 | 11/2013 | Neuberger et al. |
| 2013/0317519 A1 | 11/2013 | Romo et al. |
| 2013/0334281 A1 | 12/2013 | Williams |
| 2013/0345519 A1 | 12/2013 | Piskun et al. |
| 2013/0345686 A1 | 12/2013 | Brown |
| 2014/0000411 A1 | 1/2014 | Shelton, IV et al. |
| 2014/0005681 A1 | 1/2014 | Gee et al. |
| 2014/0039517 A1 | 2/2014 | Bowling |
| 2014/0039681 A1 | 2/2014 | Bowling |
| 2014/0046308 A1 | 2/2014 | Bischoff |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0066944 A1 | 3/2014 | Taylor et al. |
| 2014/0069437 A1 | 3/2014 | Reis et al. |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0163736 A1 | 6/2014 | Azizian |
| 2014/0166023 A1 | 6/2014 | Kishi |
| 2014/0171778 A1 | 6/2014 | Tsusaka |
| 2014/0180063 A1 | 6/2014 | Zhao |
| 2014/0194859 A1 | 7/2014 | Ianchulev |
| 2014/0194905 A1 | 7/2014 | Kappel |
| 2014/0222019 A1 | 8/2014 | Brudnick |
| 2014/0222207 A1 | 8/2014 | Bowling et al. |
| 2014/0243849 A1 | 8/2014 | Saglam et al. |
| 2014/0246473 A1 | 9/2014 | Auld |
| 2014/0257333 A1 | 9/2014 | Blumenkranz |
| 2014/0275956 A1 | 9/2014 | Fan |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276723 A1 | 9/2014 | Parihar |
| 2014/0276935 A1 | 9/2014 | Yu |
| 2014/0276936 A1 | 9/2014 | Kokish et al. |
| 2014/0276956 A1 | 9/2014 | Crainich |
| 2014/0277334 A1 | 9/2014 | Yu et al. |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0375784 A1 | 12/2014 | Massetti |
| 2015/0012134 A1 | 1/2015 | Robinson |
| 2015/0073439 A1 | 3/2015 | Dannaher |
| 2015/0080879 A1 | 3/2015 | Trees |
| 2015/0090063 A1 | 4/2015 | Lantermann et al. |
| 2015/0127045 A1 | 5/2015 | Prestel |
| 2015/0133960 A1 | 5/2015 | Lohmeier |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |

(56) References Cited

U.S. PATENT DOCUMENTS

| | | |
|---|---|---|
| 2015/0150635 A1 | 6/2015 | Kilroy |
| 2015/0164522 A1 | 6/2015 | Budiman |
| 2015/0182250 A1 | 7/2015 | Conlon et al. |
| 2015/0190204 A1 | 7/2015 | Popovi |
| 2015/0201917 A1 | 7/2015 | Snow |
| 2015/0202085 A1 | 7/2015 | Lemonis |
| 2015/0231364 A1 | 8/2015 | Blanchard |
| 2015/0314110 A1 | 11/2015 | Park |
| 2015/0366629 A1 | 12/2015 | Bowling |
| 2015/0374445 A1 | 12/2015 | Gombert et al. |
| 2015/0374446 A1 | 12/2015 | Malackowski |
| 2016/0000512 A1 | 1/2016 | Gombert et al. |
| 2016/0022466 A1 | 1/2016 | Pedtke |
| 2016/0030073 A1 | 2/2016 | Lsakov |
| 2016/0045208 A1 | 2/2016 | Ciulla |
| 2016/0051220 A1 | 2/2016 | Wan |
| 2016/0051318 A1 | 2/2016 | Manzo et al. |
| 2016/0066935 A1 | 3/2016 | Nguyen et al. |
| 2016/0157945 A1 | 6/2016 | Madhani |
| 2016/0158490 A1 | 6/2016 | Leeflang |
| 2016/0166234 A1 | 6/2016 | Zhang |
| 2016/0183841 A1 | 6/2016 | Duindam et al. |
| 2016/0192860 A1 | 7/2016 | Allenby |
| 2016/0199984 A1 | 7/2016 | Lohmeier et al. |
| 2016/0206389 A1 | 7/2016 | Miller |
| 2016/0213435 A1 | 7/2016 | Hourtash |
| 2016/0235495 A1 | 8/2016 | Wallace et al. |
| 2016/0242858 A1 | 8/2016 | Moctezuma de la Barrera et al. |
| 2016/0249932 A1 | 9/2016 | Rogers et al. |
| 2016/0270865 A1 | 9/2016 | Landey et al. |
| 2016/0287279 A1 | 10/2016 | Bovay et al. |
| 2016/0302871 A1 | 10/2016 | Gregerson et al. |
| 2016/0303743 A1 | 10/2016 | Rockrohr |
| 2016/0310146 A1 | 10/2016 | Levy et al. |
| 2016/0331358 A1 | 11/2016 | Gordon |
| 2016/0338783 A1 | 11/2016 | Romo et al. |
| 2016/0346049 A1 | 12/2016 | Allen et al. |
| 2016/0367324 A1 | 12/2016 | Sato et al. |
| 2017/0000577 A1 | 1/2017 | Bowling |
| 2017/0007337 A1 | 1/2017 | Dan |
| 2017/0020615 A1 | 1/2017 | Koenig et al. |
| 2017/0049471 A1 | 2/2017 | Gaffney et al. |
| 2017/0055995 A1 | 3/2017 | Weier |
| 2017/0065227 A1 | 3/2017 | Marrs |
| 2017/0071584 A1 | 3/2017 | Suigetsu et al. |
| 2017/0086934 A1 | 3/2017 | Devengenzo et al. |
| 2017/0095234 A1 | 4/2017 | Prisco et al. |
| 2017/0095295 A1 | 4/2017 | Overmyer |
| 2017/0135706 A1 | 5/2017 | Frey |
| 2017/0151028 A1 | 6/2017 | Ogawa et al. |
| 2017/0151416 A1 | 6/2017 | Kutikov |
| 2017/0165009 A1 | 6/2017 | Chaplin et al. |
| 2017/0172553 A1 | 6/2017 | Chaplin |
| 2017/0172680 A1 | 6/2017 | Bowling |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0258534 A1 | 9/2017 | Hourtash et al. |
| 2017/0265923 A1 | 9/2017 | Privitera |
| 2017/0265954 A1 | 9/2017 | Burbank |
| 2017/0281049 A1 | 10/2017 | Yamamoto |
| 2017/0290631 A1 | 10/2017 | Lee et al. |
| 2017/0319289 A1 | 11/2017 | Neff et al. |
| 2017/0325932 A1 | 11/2017 | Hoelzle |
| 2017/0333147 A1 | 11/2017 | Bernstein |
| 2018/0000563 A1 | 1/2018 | Shanjani et al. |
| 2018/0025666 A1 | 1/2018 | Ho et al. |
| 2018/0042464 A1 | 2/2018 | Arai |
| 2018/0042686 A1 | 2/2018 | Peine |
| 2018/0049792 A1 | 2/2018 | Eckert |
| 2018/0049824 A1 | 2/2018 | Harris |
| 2018/0056044 A1 | 3/2018 | Choi et al. |
| 2018/0079090 A1 | 3/2018 | Koenig et al. |
| 2018/0080841 A1 | 3/2018 | Cordoba |
| 2018/0104820 A1 | 4/2018 | Troy et al. |
| 2018/0116735 A1 | 5/2018 | Tierney et al. |
| 2018/0140371 A1 | 5/2018 | Hares et al. |
| 2018/0193049 A1 | 7/2018 | Heck et al. |
| 2018/0206927 A1 | 7/2018 | Prisco et al. |
| 2018/0206931 A1 | 7/2018 | Scheib |
| 2018/0221038 A1 | 8/2018 | Noonan et al. |
| 2018/0221039 A1 | 8/2018 | Shah |
| 2018/0243048 A1 | 8/2018 | Shan |
| 2018/0250085 A1 | 9/2018 | Simi |
| 2018/0279852 A1 | 10/2018 | Rafii-Tari et al. |
| 2018/0289431 A1 | 10/2018 | Draper et al. |
| 2018/0296285 A1 | 10/2018 | Simi et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0326181 A1 | 11/2018 | Kokish et al. |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0015166 A1 | 1/2019 | Mahoney |
| 2019/0069962 A1 | 3/2019 | Tabandeh et al. |
| 2019/0099231 A1 | 4/2019 | Bruehwiler |
| 2019/0099232 A1 | 4/2019 | Soto et al. |
| 2019/0110839 A1 | 4/2019 | Rafii-Tari et al. |
| 2019/0117320 A1 | 4/2019 | Shoham et al. |
| 2019/0117324 A1 | 4/2019 | Hibner |
| 2019/0151148 A1 | 4/2019 | Alvarez et al. |
| 2019/0125465 A1 | 5/2019 | Evans et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175287 A1 | 6/2019 | Hill |
| 2019/0183585 A1 | 6/2019 | Rafii-Tari et al. |
| 2019/0183587 A1 | 6/2019 | Rafii-Tari et al. |
| 2019/0192249 A1 | 6/2019 | Bowling |
| 2019/0216548 A1 | 7/2019 | Ummalaneni |
| 2019/0216576 A1 | 7/2019 | Eyre |
| 2019/0223967 A1 | 7/2019 | Abbott |
| 2019/0223974 A1 | 7/2019 | Romo |
| 2019/0231458 A1 | 8/2019 | DiMaio |
| 2019/0231460 A1 | 8/2019 | DiMaio |
| 2019/0239890 A1 | 8/2019 | Stokes |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298460 A1 | 10/2019 | Al-Jadda |
| 2019/0298464 A1 | 10/2019 | Abbott |
| 2019/0298465 A1 | 10/2019 | Chin |
| 2019/0298469 A1 | 10/2019 | Ramstad et al. |
| 2019/0314616 A1 | 10/2019 | Moll et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0008874 A1 | 1/2020 | Barbagli et al. |
| 2020/0030046 A1 | 1/2020 | Bowling |
| 2020/0038123 A1 | 2/2020 | Graetzel |
| 2020/0039086 A1 | 2/2020 | Meyer |
| 2020/0046434 A1 | 2/2020 | Graetzel |
| 2020/0085516 A1 | 3/2020 | DeFonzo |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100855 A1 | 4/2020 | Leparmentier |
| 2020/0107894 A1 | 4/2020 | Wallace |
| 2020/0121502 A1 | 4/2020 | Kintz |
| 2020/0129252 A1 | 4/2020 | Kokish |
| 2020/0138531 A1 | 5/2020 | Chaplin |
| 2020/0146769 A1 | 5/2020 | Eyre |
| 2020/0155245 A1 | 5/2020 | Yu |
| 2020/0155801 A1 | 5/2020 | Kokish |

(56) References Cited

U.S. PATENT DOCUMENTS

| | | |
|---|---|---|
| 2020/0163726 A1 | 5/2020 | Tanner |
| 2020/0170720 A1 | 6/2020 | Ummalaneni |
| 2020/0171660 A1 | 6/2020 | Ho |
| 2020/0188043 A1 | 6/2020 | Yu |
| 2020/0197109 A1 | 6/2020 | Chaplin |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0230360 A1 | 7/2020 | Yu |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |
| 2020/0383735 A1 | 12/2020 | Lewis |
| 2020/0405317 A1 | 12/2020 | Wallace |
| 2020/0405411 A1 | 12/2020 | Draper et al. |
| 2020/0405413 A1 | 12/2020 | Kokish |
| 2020/0405419 A1 | 12/2020 | Mao |
| 2020/0405420 A1 | 12/2020 | Purohit |
| 2020/0405423 A1 | 12/2020 | Schuh |
| 2020/0405424 A1 | 12/2020 | Schuh |
| 2020/0405434 A1 | 12/2020 | Schuh |
| 2020/0406002 A1 | 12/2020 | Romo |

FOREIGN PATENT DOCUMENTS

| | | |
|---|---|---|
| CN | 100515347 | 7/2009 |
| CN | 103037799 | 4/2011 |
| CN | 201884596 U | 6/2011 |
| CN | 102316817 | 1/2012 |
| CN | 102327118 | 1/2012 |
| CN | 102458295 | 5/2012 |
| CN | 102665590 | 9/2012 |
| CN | 102834043 | 12/2012 |
| CN | 102973317 | 3/2013 |
| CN | 102015759 | 4/2013 |
| CN | 103298414 | 9/2013 |
| CN | 103735313 | 4/2014 |
| CN | 104619281 | 5/2015 |
| CN | 105147393 | 12/2015 |
| CN | 105559850 | 5/2016 |
| CN | 105559886 | 5/2016 |
| CN | 205729413 | 11/2016 |
| DE | 19649082 | 1/1998 |
| DE | 102004020465 | 9/2005 |
| EP | 1321 106 | 6/2003 |
| EP | 1 442 720 | 8/2004 |
| EP | 1 849 423 | 10/2007 |
| EP | 2 567 670 | 3/2013 |
| EP | 3 025 630 | 6/2016 |
| JP | 07-136173 | 5/1995 |
| JP | 2005-270464 | 10/2005 |
| JP | 2009-139187 | 6/2009 |
| JP | 2010-046384 | 3/2010 |
| JP | 2014-159071 | 9/2014 |
| JP | 2015-181495 | 10/2015 |
| WO | WO 94/14494 | 7/1994 |
| WO | WO 96/22591 | 7/1996 |
| WO | WO 02/74178 | 9/2002 |
| WO | WO 07/146987 | 12/2007 |
| WO | WO 09/092059 | 7/2009 |
| WO | WO 10/133982 | 11/2010 |
| WO | WO 11/005335 | 1/2011 |
| WO | WO 11/161218 | 12/2011 |
| WO | WO 12/037506 | 3/2012 |
| WO | WO 13/107468 | 7/2013 |
| WO | WO 13/179600 | 12/2013 |
| WO | WO 15/127231 | 8/2015 |
| WO | WO 15/153174 | 10/2015 |
| WO | WO 16/137612 | 9/2016 |
| WO | WO 17/059412 | 4/2017 |
| WO | WO 17/114855 | 7/2017 |
| WO | WO 17/151993 | 9/2017 |
| WO | WO 18/069679 | 4/2018 |
| WO | WO 18/094191 | 5/2018 |
| WO | WO 18/189722 | 10/2018 |

OTHER PUBLICATIONS

International search report and written opinion dated Jan. 6, 2021 in application No. PCT/IB2020/059010.

Hernansanz et al, 2015, A multi-robot cooperation strategy for dexterous task oriented teleoperation, 2015, Elsevier, Robotics and Autonomous Systems, 68(205):156-172.

Mayo Clinic, Robotic Surgery, https://www.mayoclinic.org/tests-procedures/robotic-surgery/about/pac-20394974?p=1, downloaded from the internet on Jul. 12, 2018, 2 pp.

\* cited by examiner

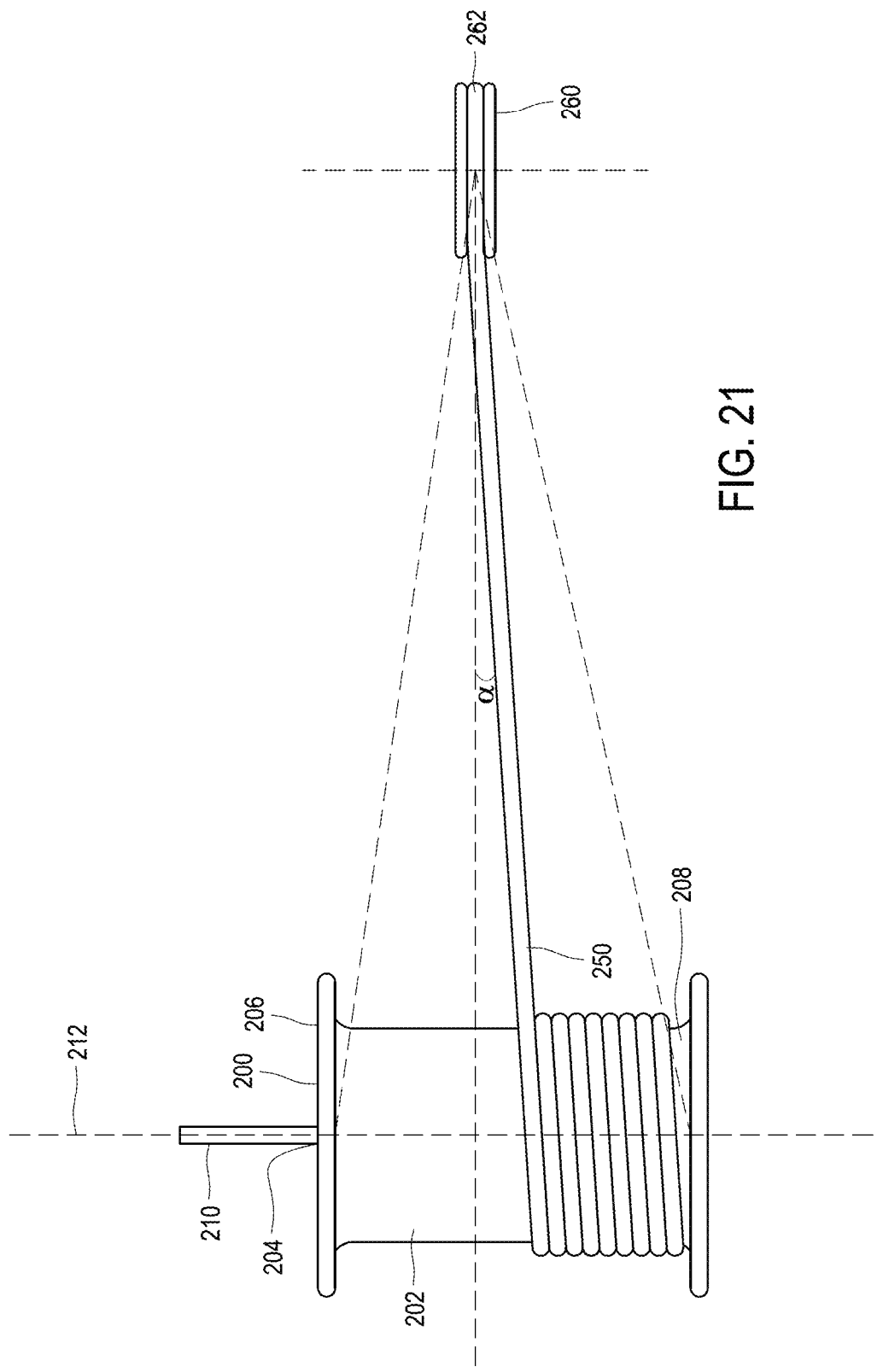

MEDICAL INSTRUMENT WITH A CAPSTAN

CROSS-REFERENCE TO RELATED APPLICATION(S)

This application claims the benefit of U.S. Provisional Application No. 62/908,446, filed Sep. 30, 2019, which is hereby incorporated by reference in its entirety.

TECHNICAL FIELD

The systems and methods disclosed herein are directed to medical instrument systems, and more particularly, to medical instruments that utilize a capstan.

BACKGROUND

Medical procedures, such as endoscopy, may involve accessing and visualizing the inside of a patient's anatomy for diagnostic and/or therapeutic purposes. For example, gastroenterology, urology, and bronchology involve medical procedures that allow a physician to examine patient lumens, such as the ureter, gastrointestinal tract, and airways (bronchi and bronchioles). During these procedures, a thin, flexible tubular tool or instrument, such as an endoscope, and/or a thin, rigid tool or instrument, such as a scope, is inserted into the patient through an orifice (such as a natural orifice) and advanced towards a tissue site identified for subsequent diagnosis and/or treatment. The medical instrument can be controllable and articulable to facilitate navigation through the anatomy.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 21 illustrates a cable connected to a capstan and a pulley.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
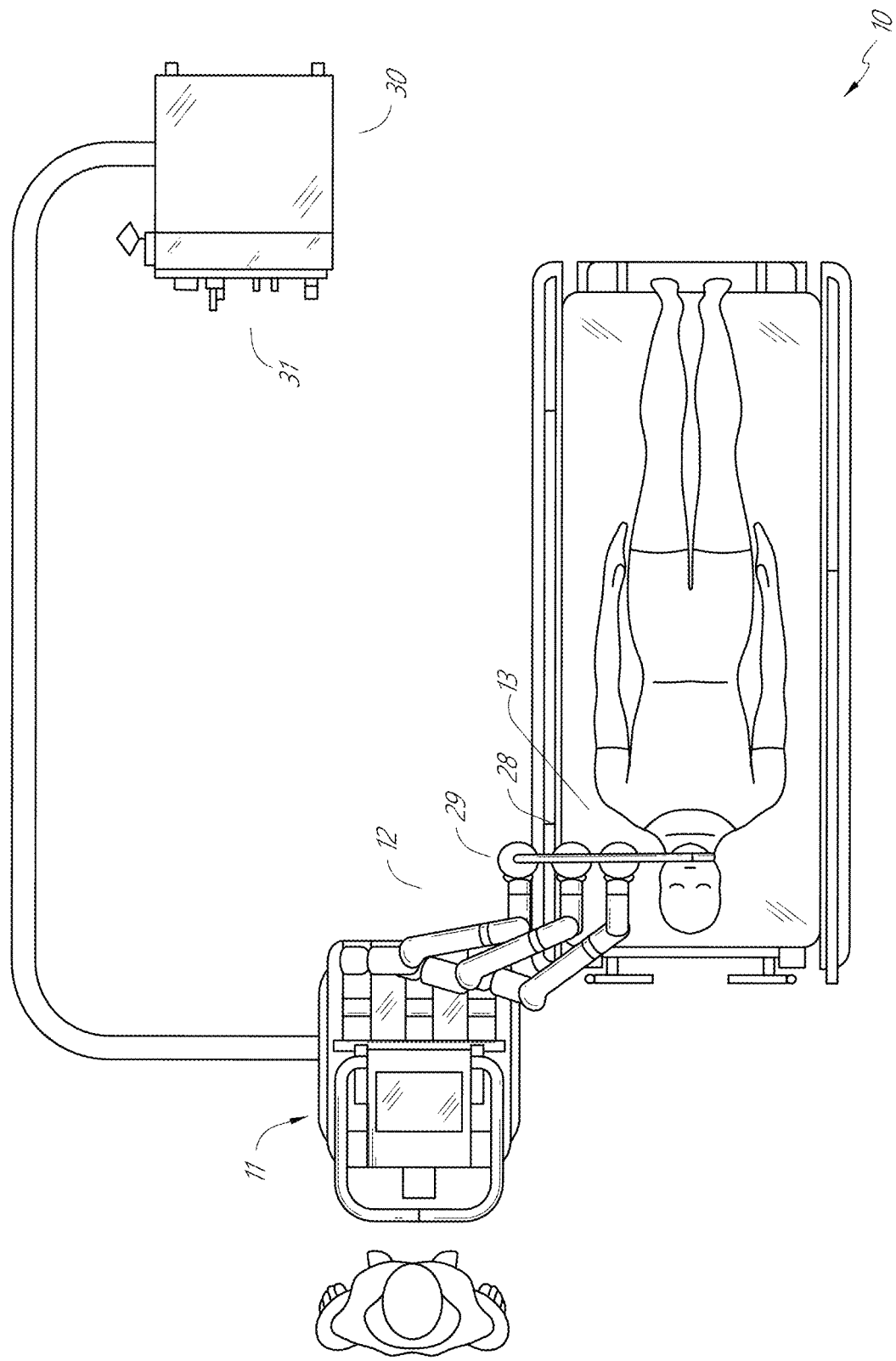
FIG. 1 illustrates an embodiment of a cart-based robotic system arranged for diagnostic and/or therapeutic bronchoscopy.
Figure 2:
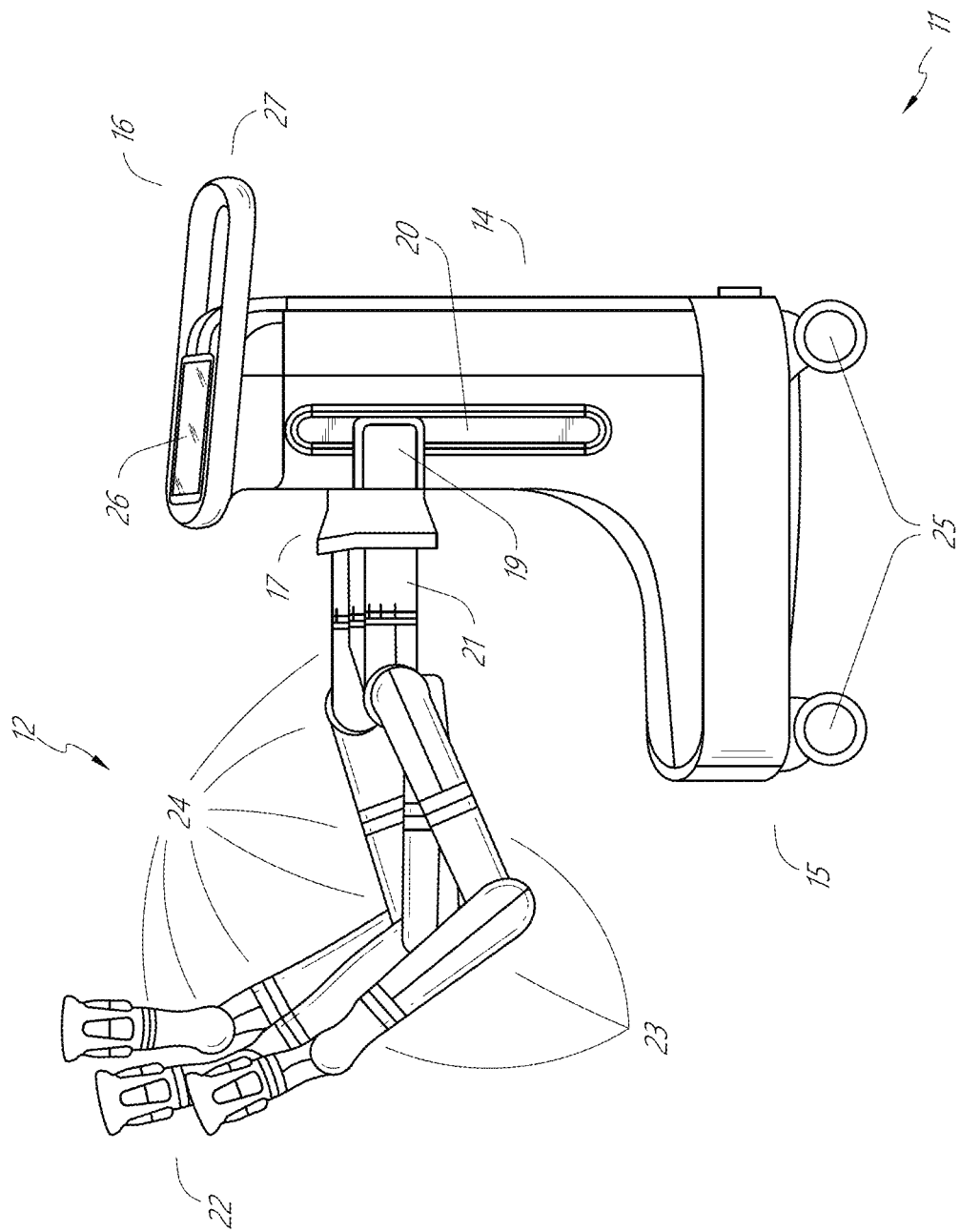
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
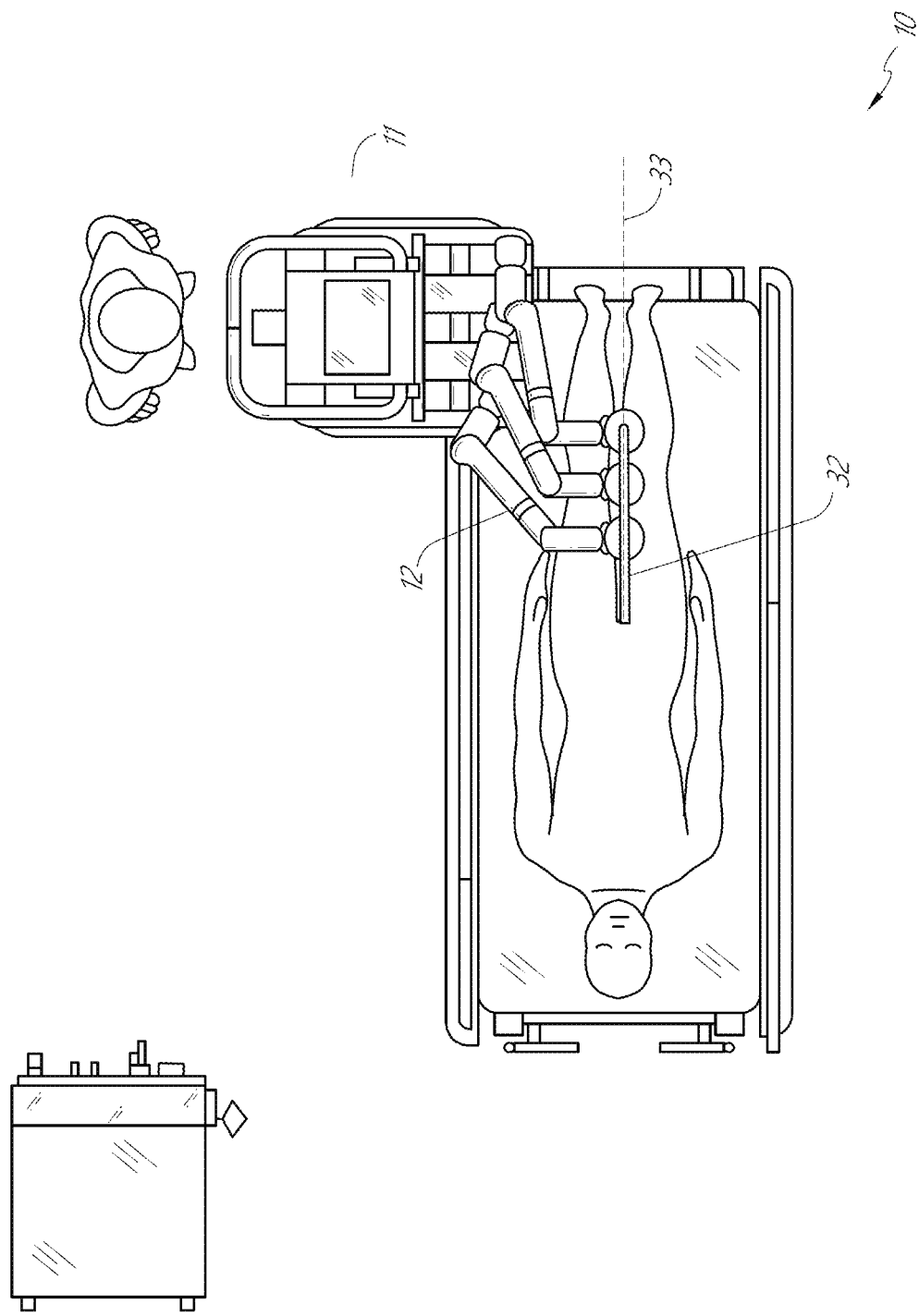
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
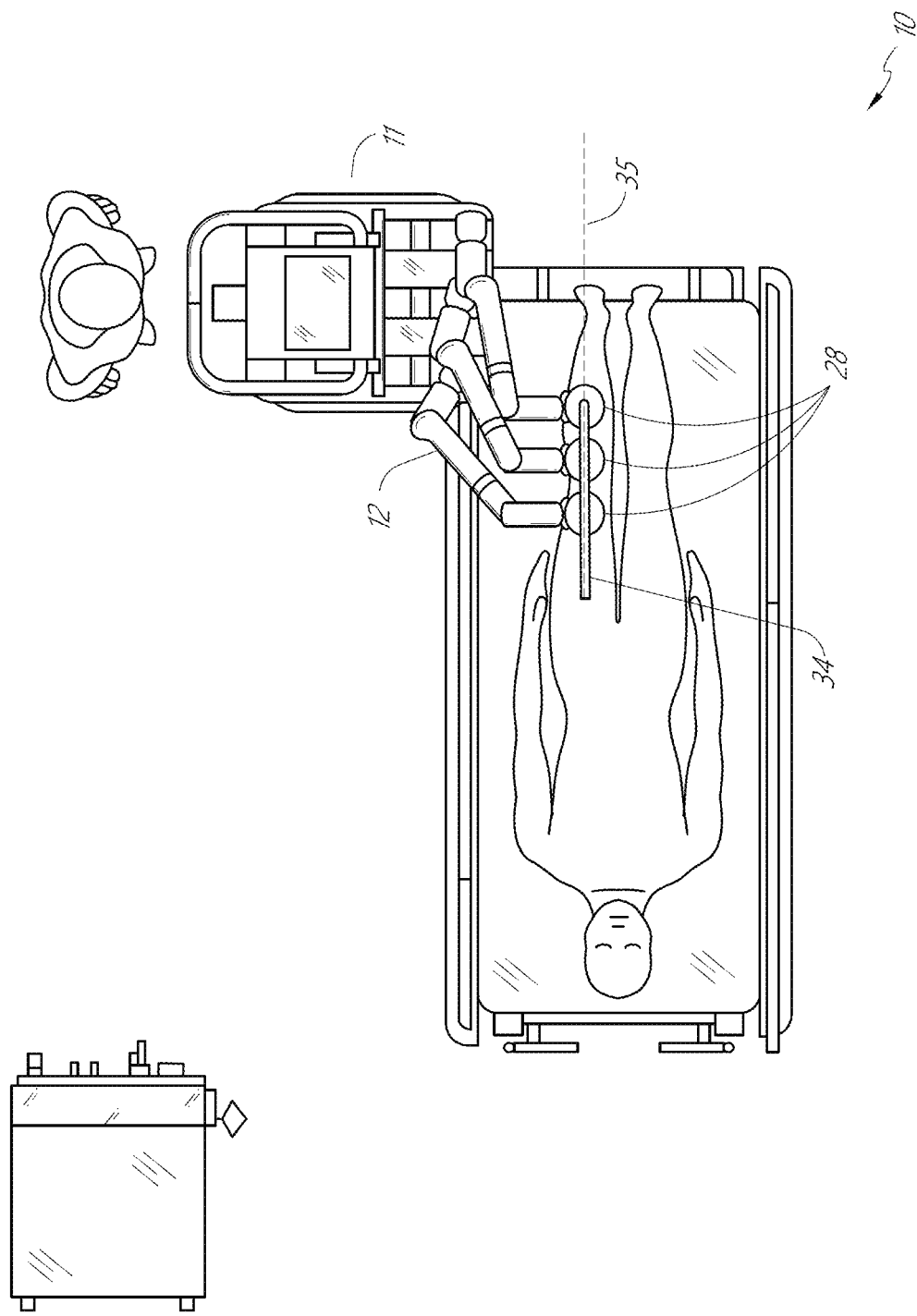
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
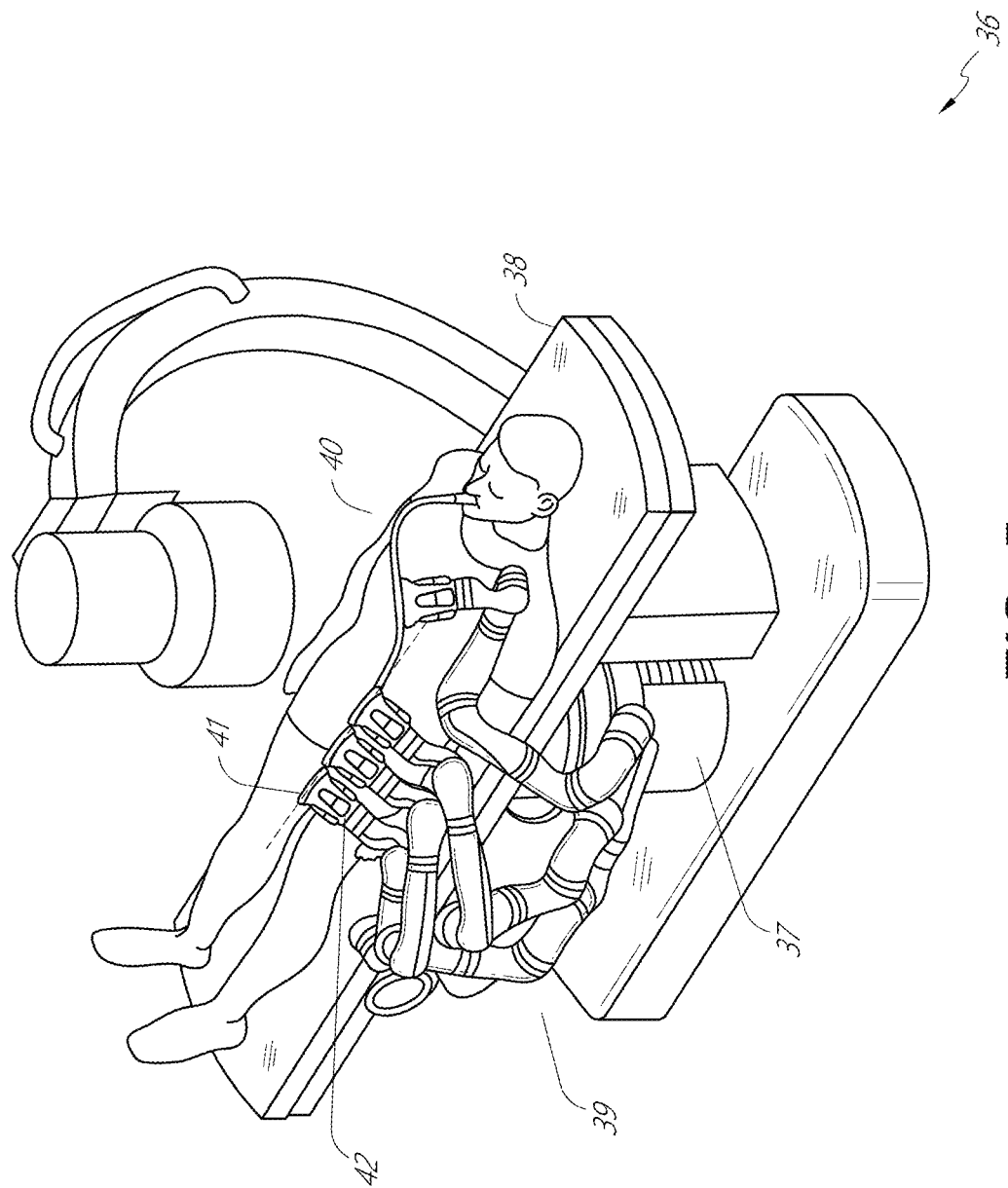
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
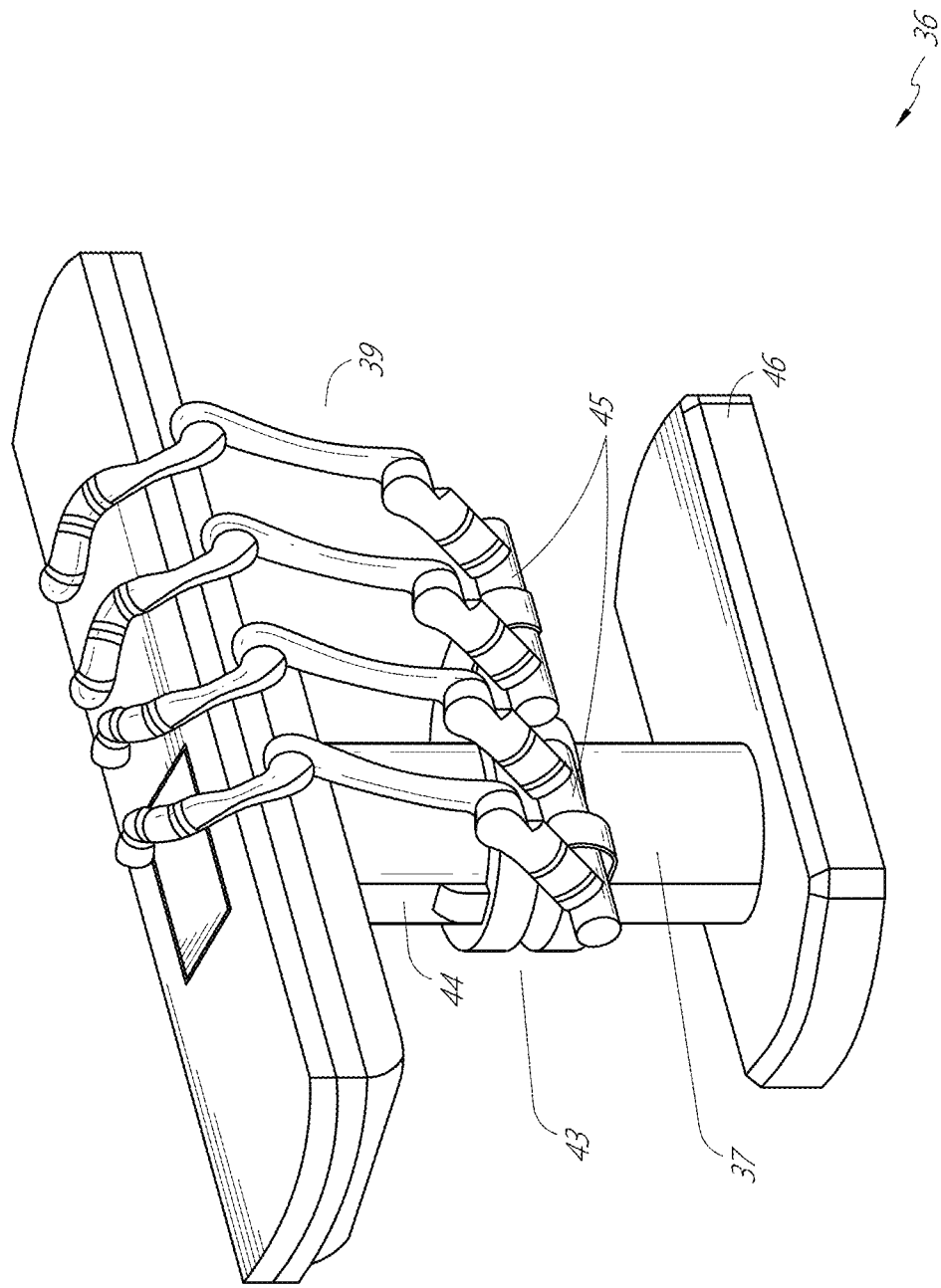
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
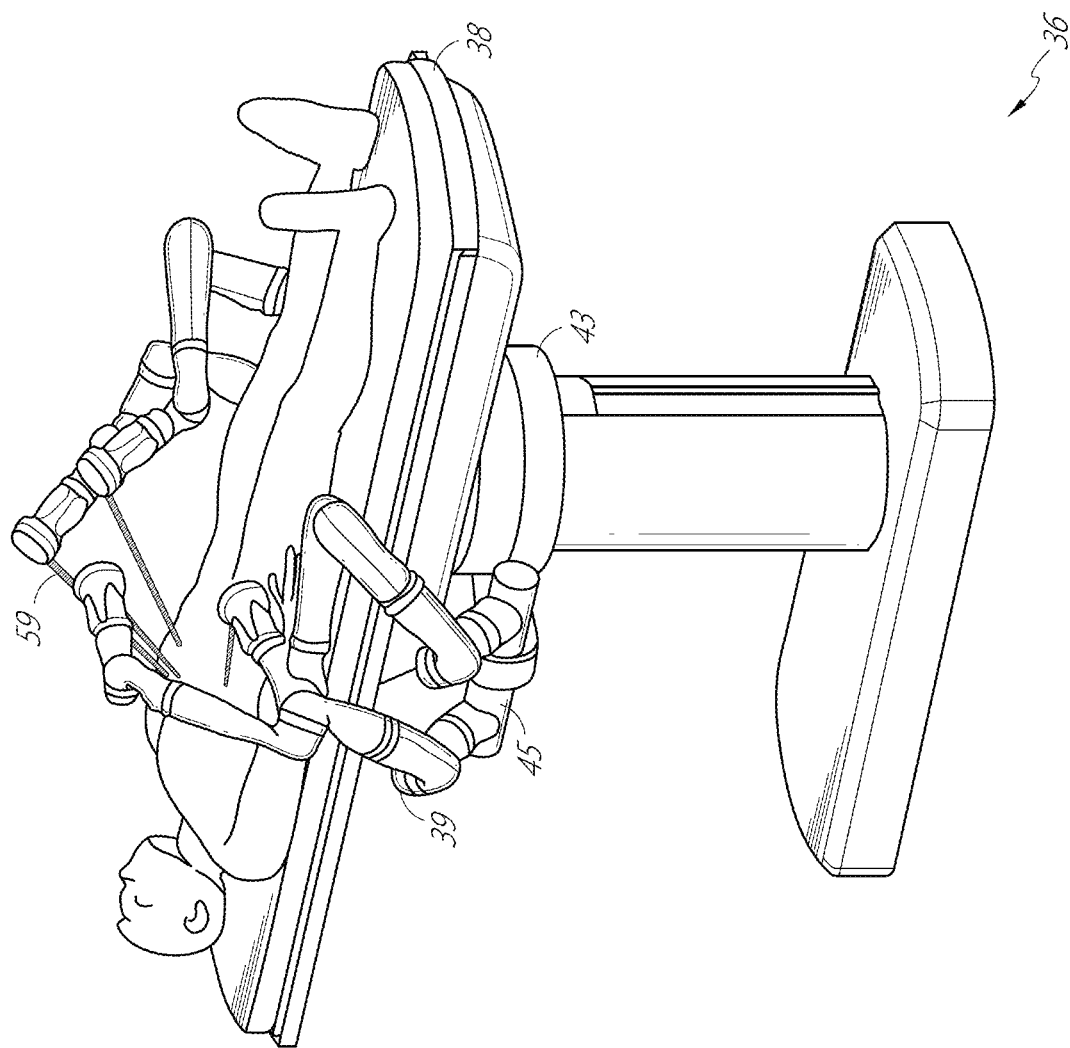
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
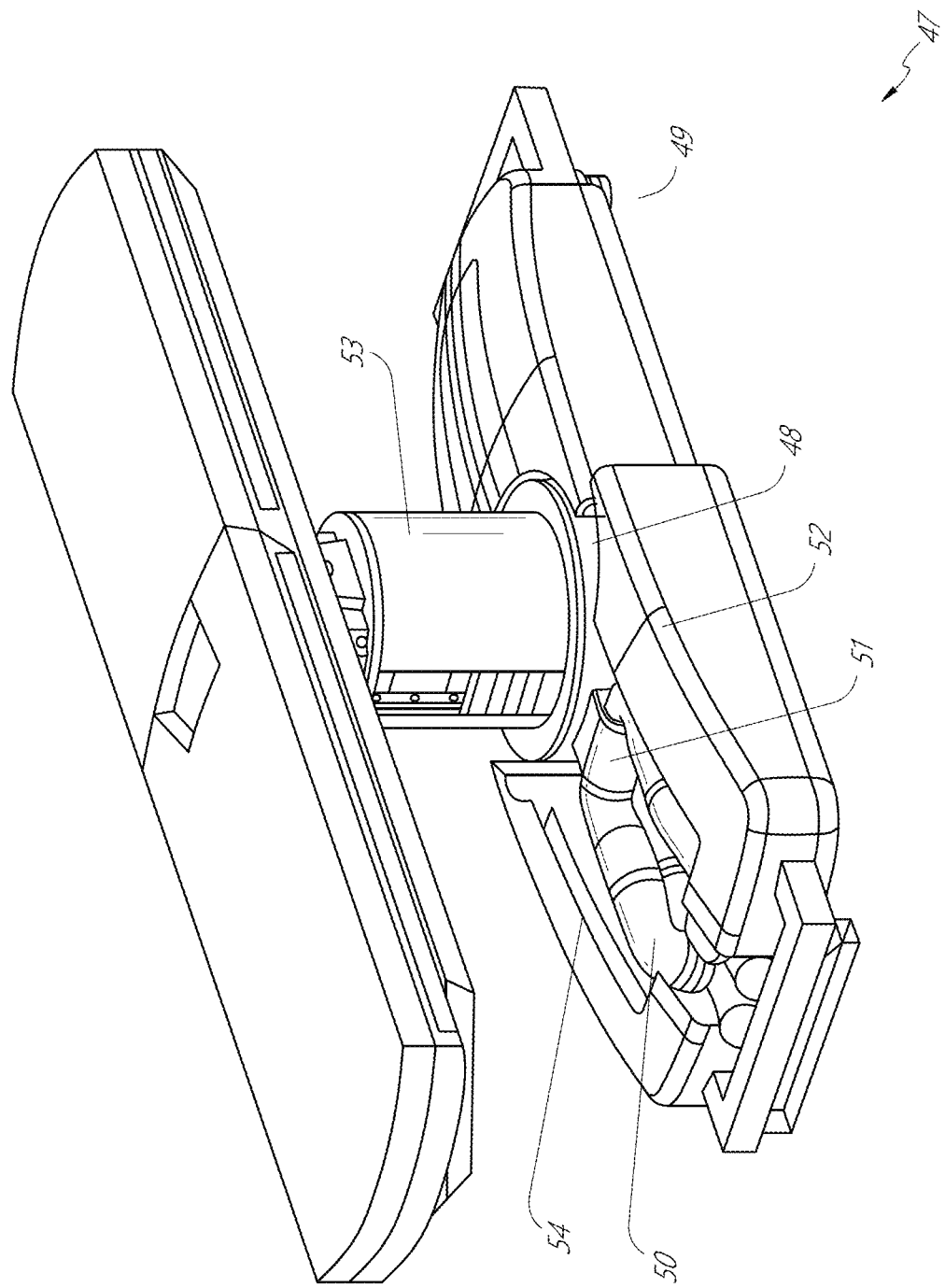
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
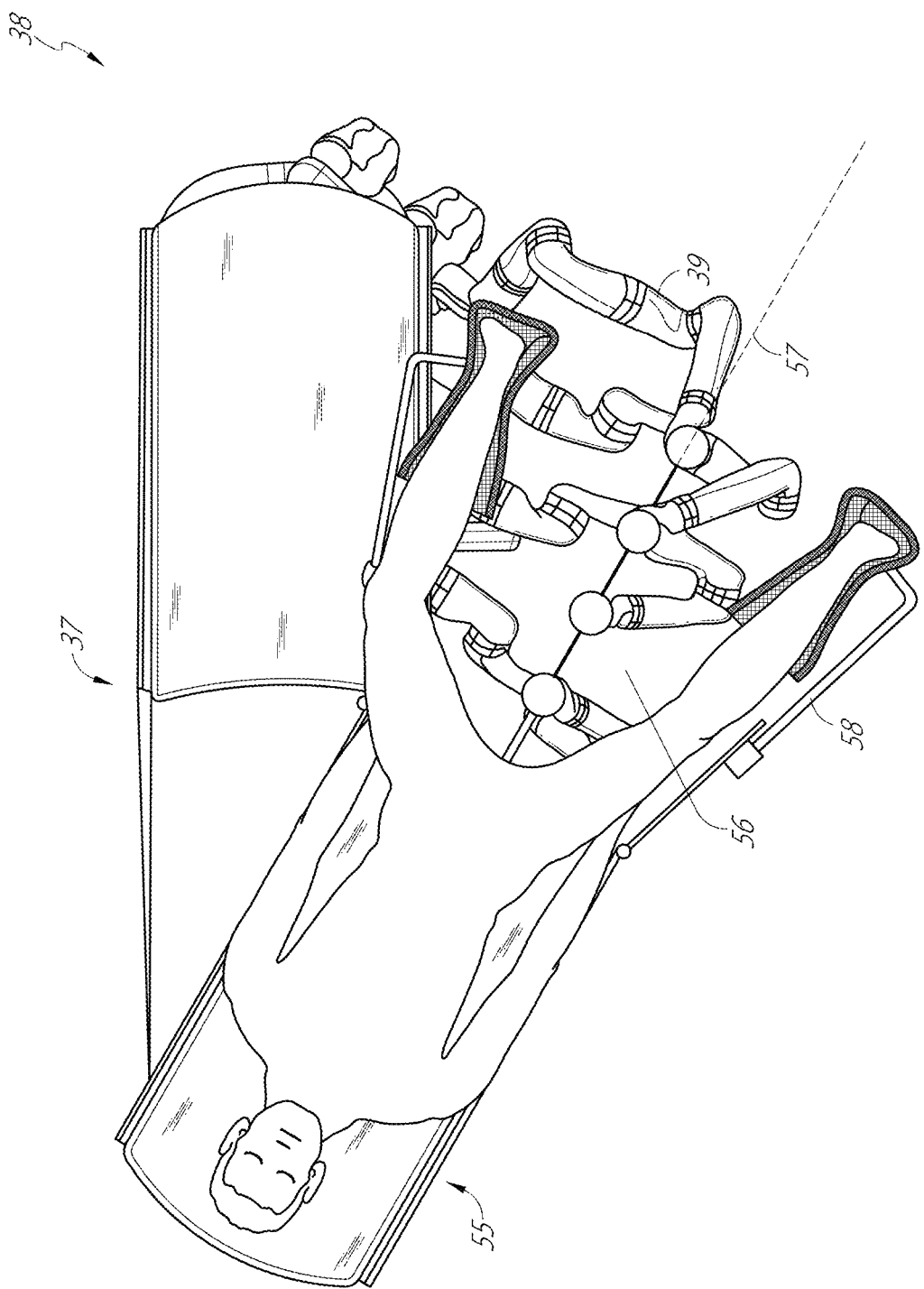
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
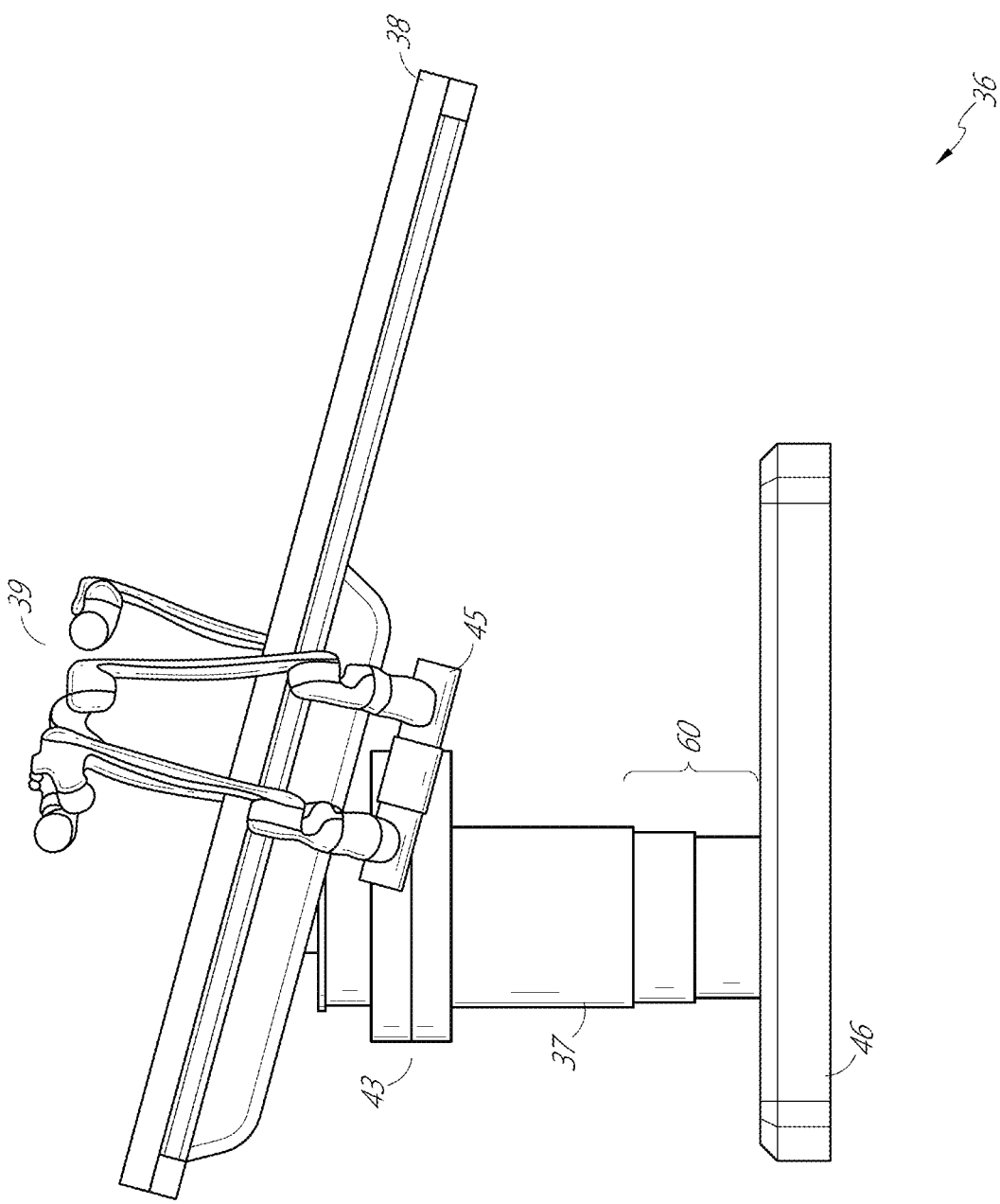
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
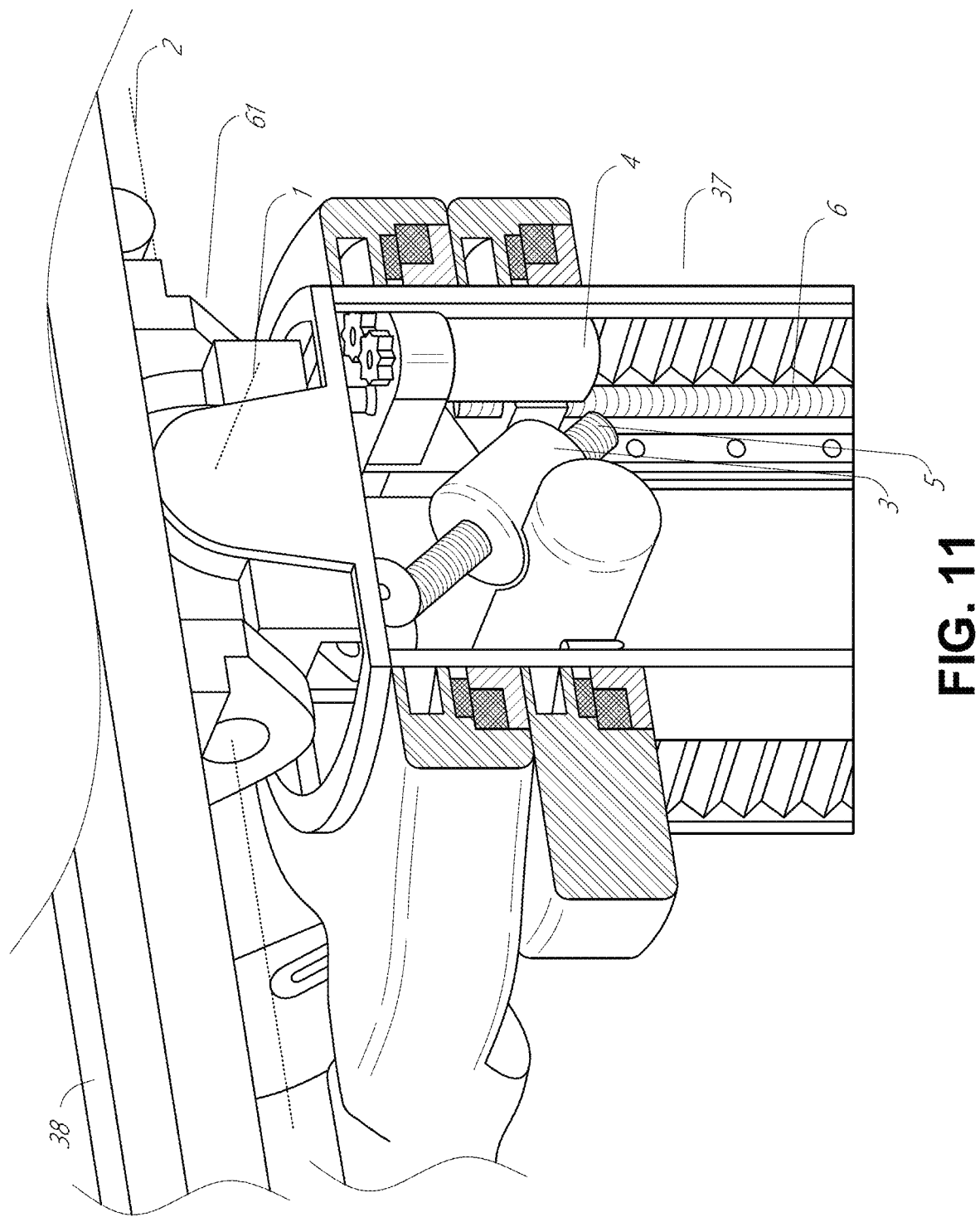
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
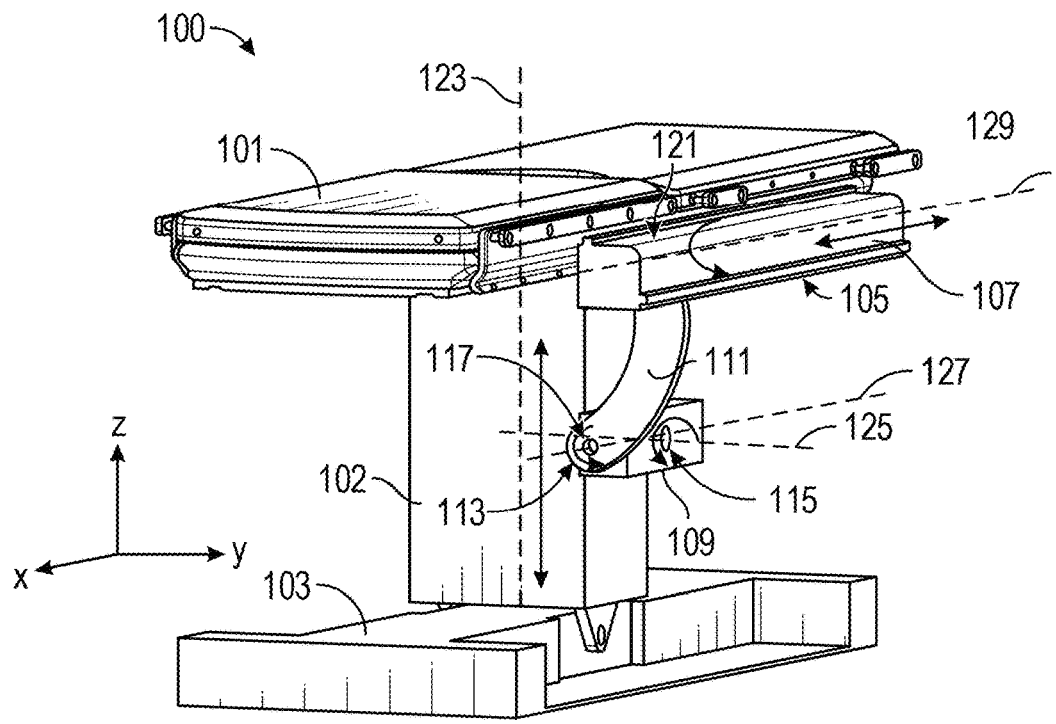
FIG. 12 illustrates an alternative embodiment of a table-based robotic system.
Figure 13:
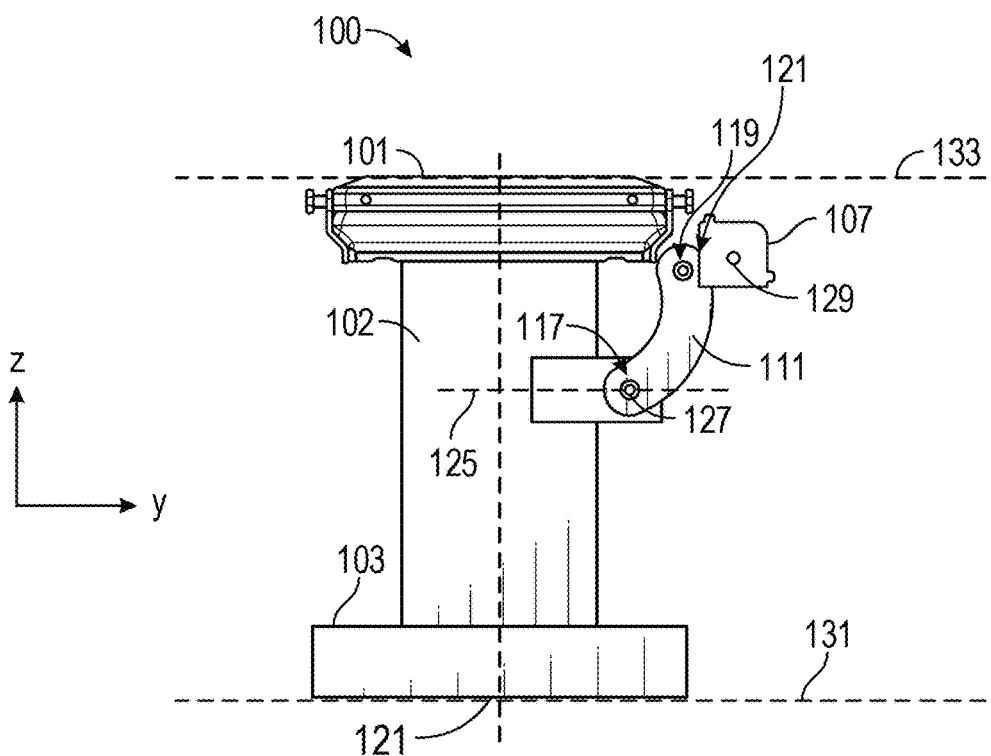
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt)

for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
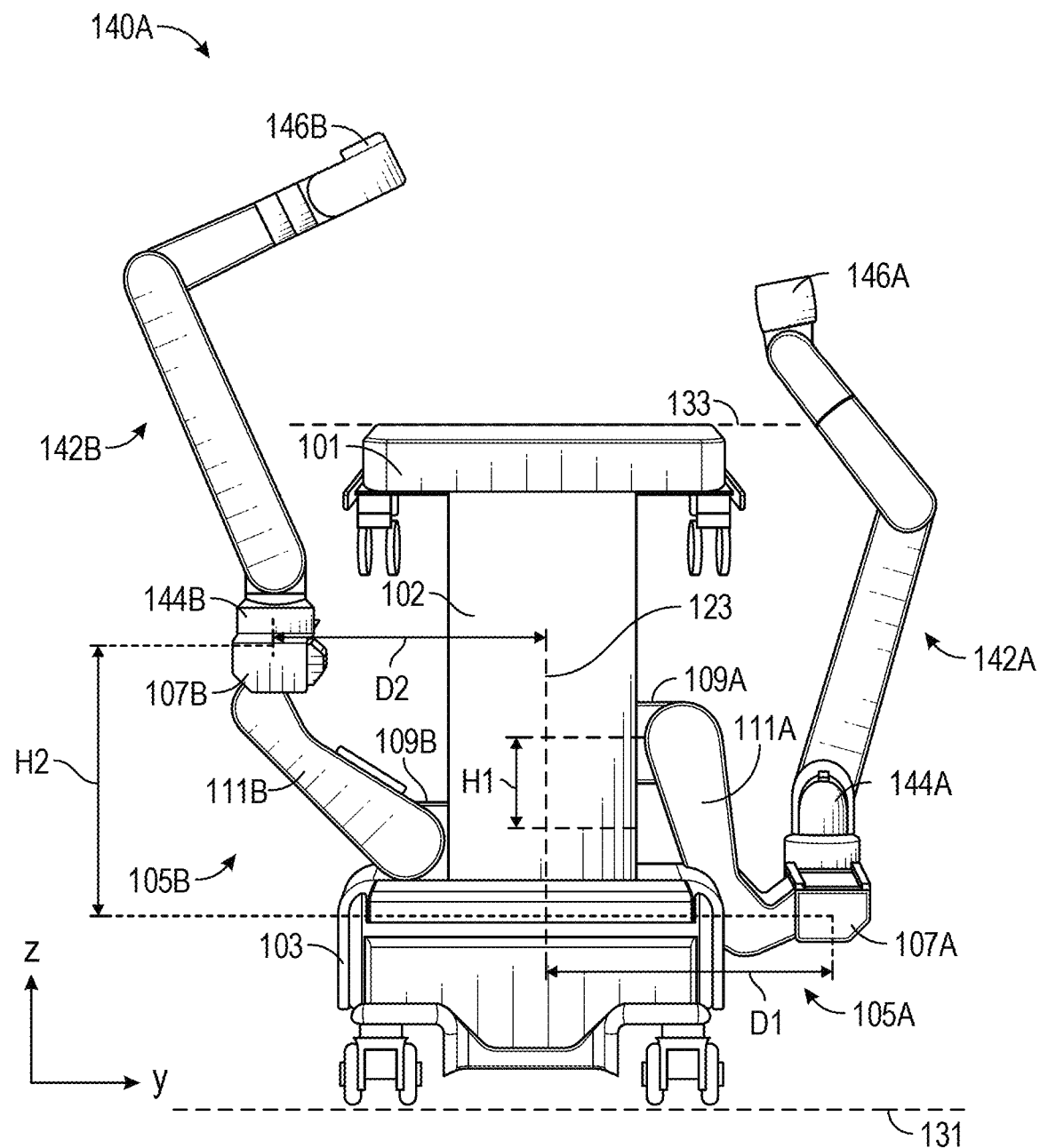
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
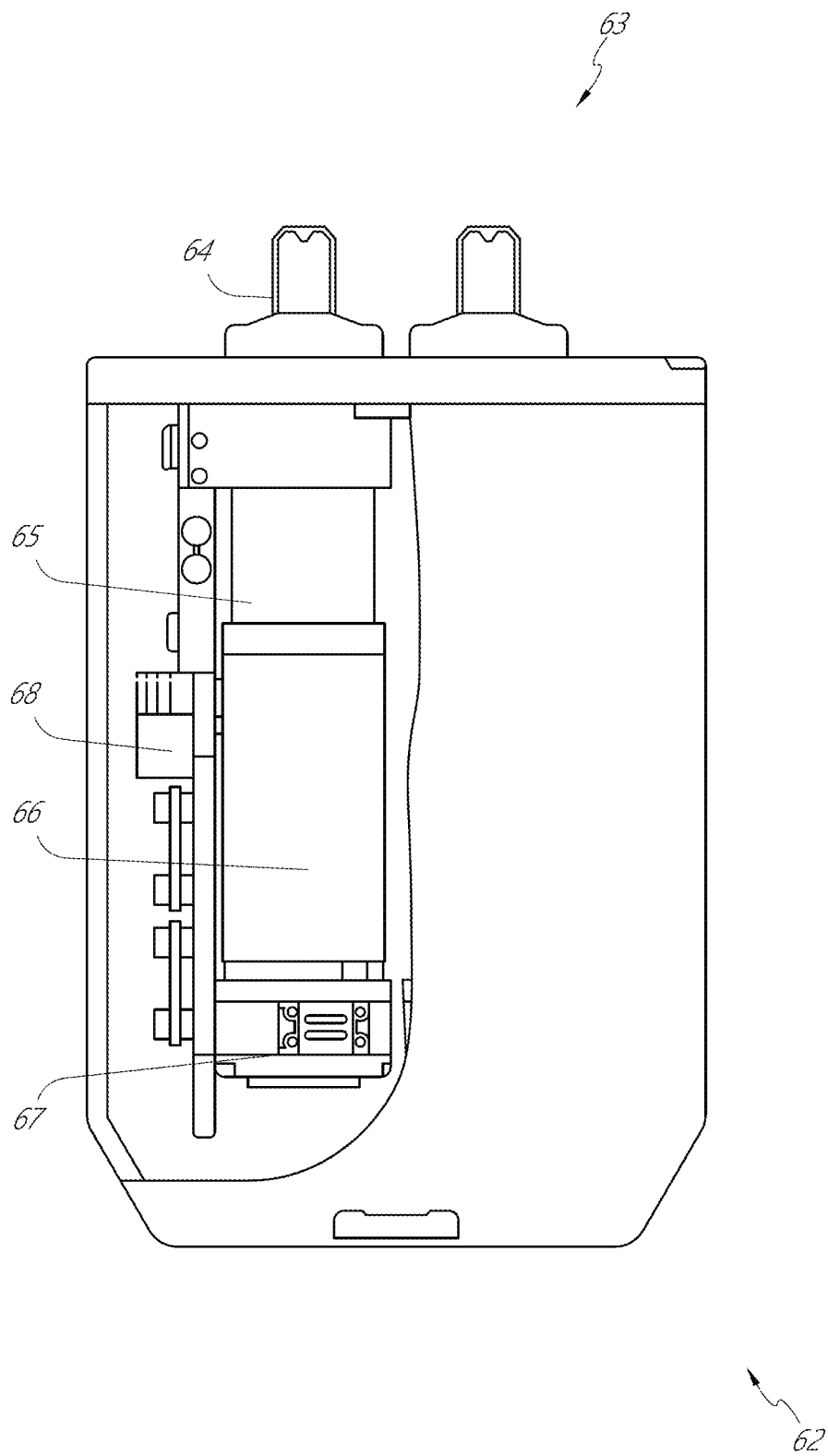
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
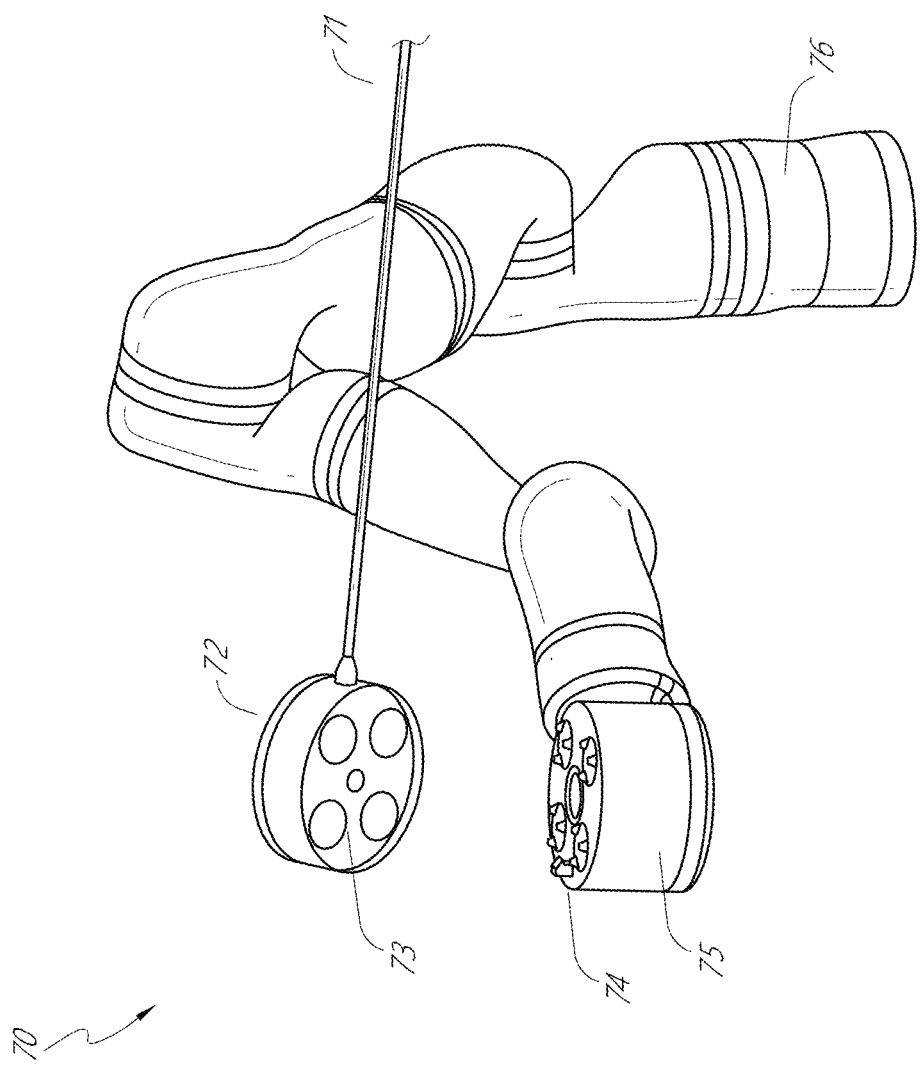
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
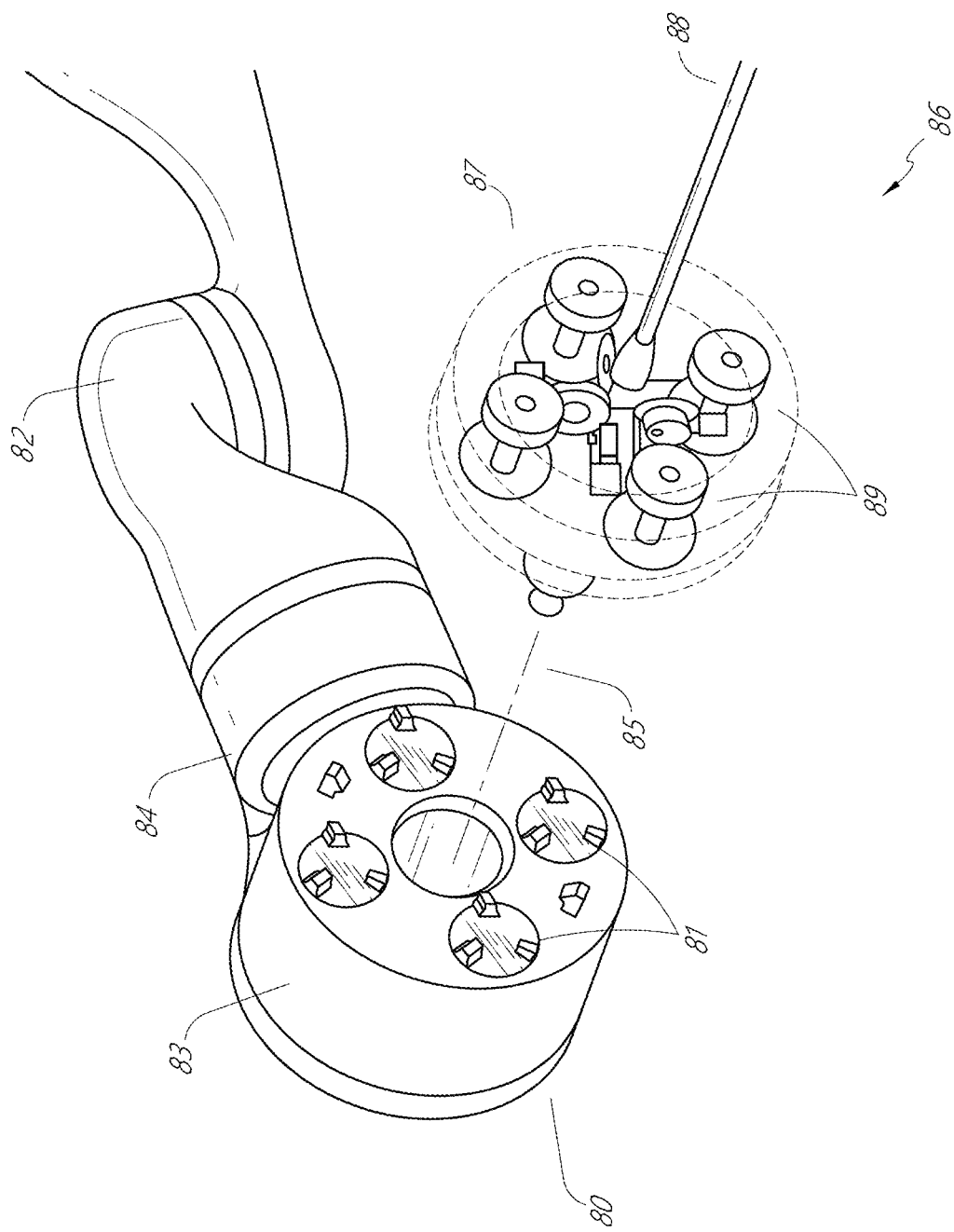
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
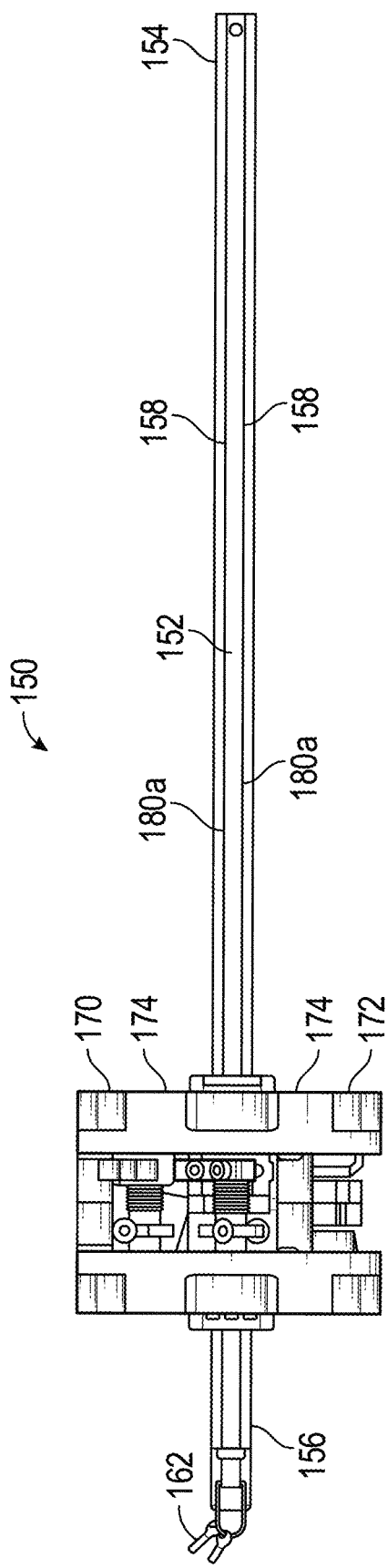
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
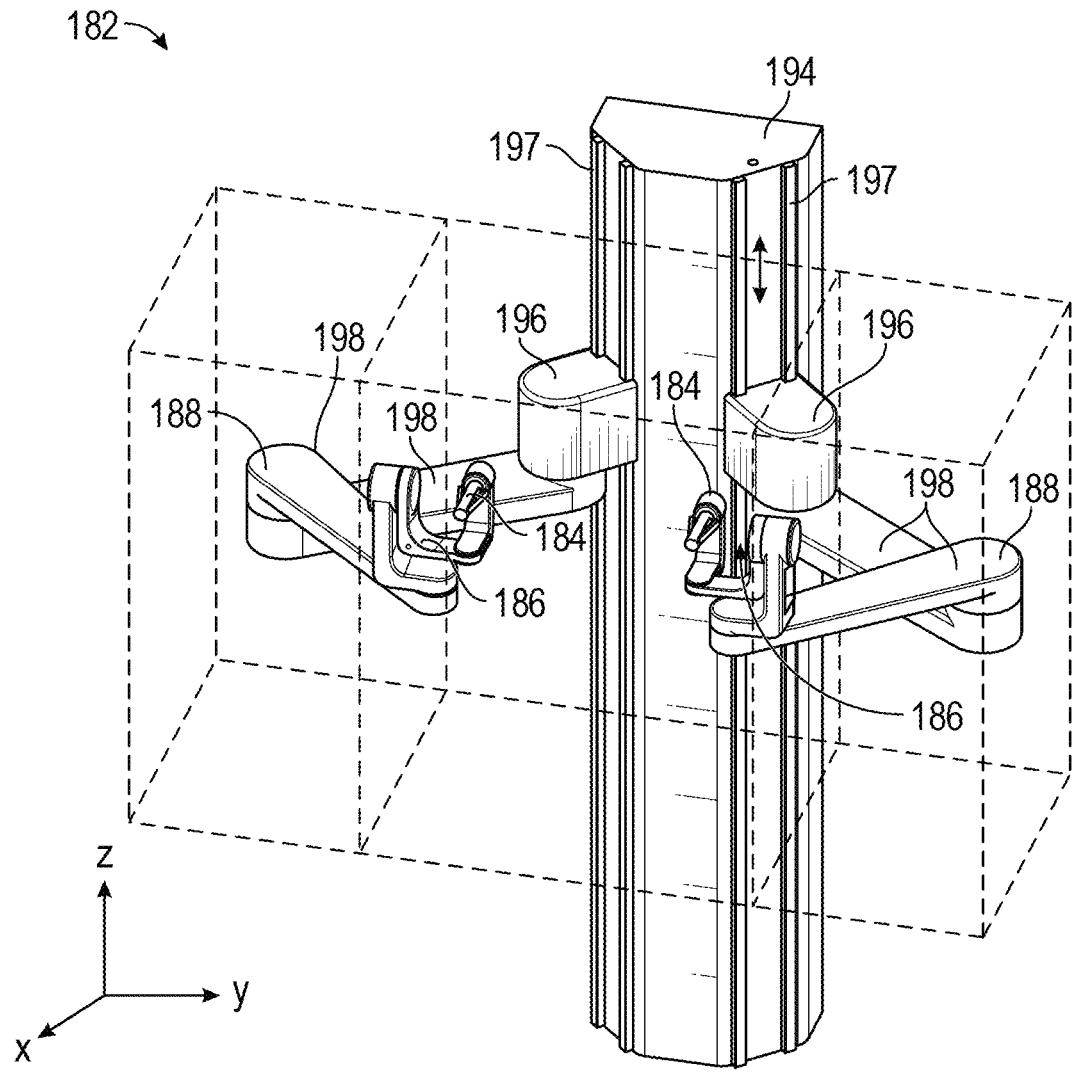
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
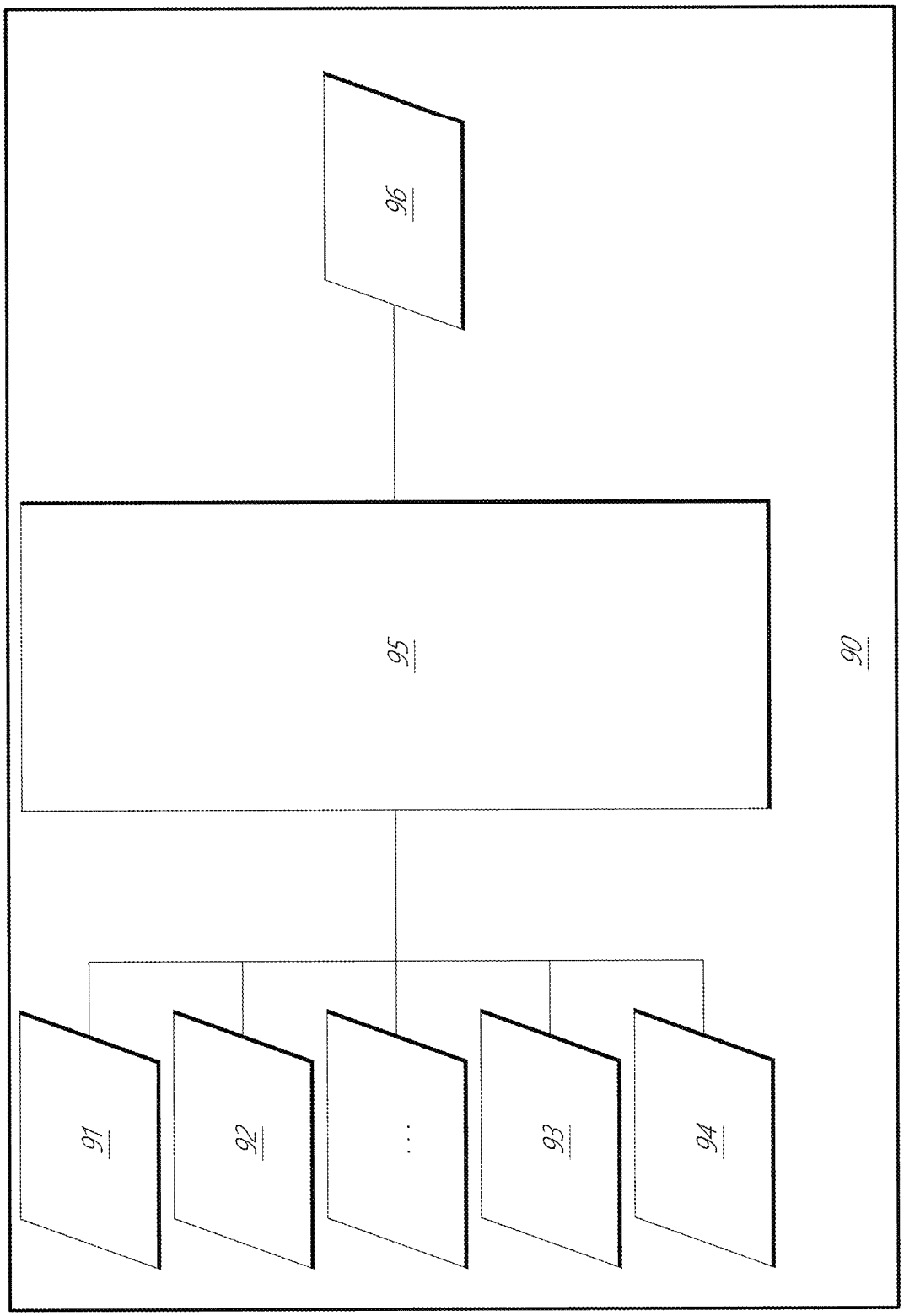
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as centerline geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, issued as U.S. Pat. No. 9,763,741 on Sep. 19, 2017, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Controlled Fleet Angle Capstan

Examples of the disclosure relate to systems and techniques for manual and/or robotic controllable medical instruments. The controllable medical instruments can be used, in some aspects, with robotically-enabled medical systems, such as those described above with reference to FIGS. 1-20. Examples of medical instruments can include a robotic arm or an instrument configured to be controlled by a robotic arm such as a flexible endoscope. In some aspects, the medical instrument can include a medical tool actuated with a wrist, a camera (e.g., with an optical fiber), a basketing tool, a blade tool, a laser tool (e.g., with an optical fiber), and/or other instruments described herein. In some aspects, the medical instruments can be configured for endoscopic procedures. For example, the medical instruments can be configured for uroscopy, ureteroscopy, gastroscopy, bronchoscopy, or other endoscopic procedures. In some examples, the medical instruments can be configured for laparoscopic procedures or other types of medical procedures (e.g., open procedures).

The medical instrument can be attached to an instrument drive mechanism or instrument driver that is positioned on the end of a robotic arm or other instrument positioning device. The instrument drive mechanism can include one or more robotic drive outputs that engage one or more robotic drive inputs or drive shafts to robotically control the medical instrument.

In some aspects, the medical instrument can be flexible tubular tool or instrument, such as an endoscope, and/or a rigid tool or instrument, such as a scope. In some aspects, the medical instrument can include a rigid tool with a wrist and the wrist can be actuated to control and manipulate the tool.

In some aspects, the medical instrument includes a flexible elongate shaft that can be deflected in various directions. In some aspects, the medical instrument can include an instrument handle, which can include one or more rotational drive inputs or drive shafts. The drive shafts may actuate one or more pullwires with one or more capstans and/or pulleys. The one or more pullwires may be actuated to articulate an elongated shaft or the wrist of the tool. The one or more pullwires may also be actuated to deflect, rotate, or translate an elongate shaft relative to the instrument handle. Controlling the articulation of the elongated shaft can include linearly translating the elongated shaft, deflecting or bending an articulable portion of the elongated shaft and in certain embodiments the roll or rotation of the elongated shaft about a longitudinal axis of the shaft. In some aspects, the articulable portion can be a distal portion of the elongated shaft. The articulable portion may be articulable in one or more degrees of freedom. Degrees of freedom may be linear or rotational. Actuation of the elongated shaft may be controlled at the instrument base with the use of one or more capstans and/or pulleys.

An instrument base or handle can be connected to the elongate shaft, such as at the proximal portion or distal portion of the shaft. The instrument base can include one or more rotational drive inputs. The rotational drive inputs may also be called drive inputs, inputs, drive shafts, rotational drive shafts, or shafts. The drive inputs may be located in a handle of the medical instrument. The elongate shaft can be coupled to the drive input to control articulation of one or more portions of the elongate shaft. The elongated shaft can include one or more pull wires which extend along the length of the elongated shaft. The one or more pull wires can be actuable to articulate the elongated shaft. The one or more drive inputs, coupled to one or more pull wires with one or more capstans/pulleys, can be configured to translate the shaft or bend the shaft in various directions.

As described above (for example, with reference to FIGS. 15-18), in some aspects, the medical instrument can include one or more pull wires extending on or through the elongated shaft. The pull wires can be attached to actuation mechanisms, such as one or more pulleys and/or capstans, within the instrument handle. The actuation mechanism can, in turn, be connected to the drive inputs such that actuation of the drive inputs operates the actuation mechanisms to pull on the pull wires to cause articulation of the elongated shaft. In some aspects, one or more of the drive inputs are each connected to the same actuation mechanism (e.g., pulley, capstan, and/or capstan assembly) within the instrument handle such that the drive input can be used to actuate the same actuation mechanism.

The physician may control the medical instrument by controlling or operating drive inputs or drive shafts of the medical device. Various tools or instruments can attach to the device driver. Insertion of an instrument (e.g., towards a surgical site) can be facilitated by the design and architecture of the instrument. For example, in some aspects, wherein an instrument includes an elongated shaft and a handle, the use of a capstan and/or pulleys can actuate the elongated shaft to translate relative to the handle along an axis of insertion. In some aspects, the use of a capstan and/or pulleys enables deflection of an elongated shaft or articulation of a wrist of a surgical tool (e.g. a cutter, a gripper, or any other tool).

It can be advantageous to route and control one or more wires or cable on a capstan. The one or more cables on the capstan can then be connected to one or pulleys. The capstan and/or the one or more pulleys may be rotated by one or more drive shafts.

FIG. 21 illustrates a cable or wire 250 connected to a capstan 200 and a pulley 260. The capstan 200 can be supported about a rotational axis. The capstan 200 may also be considered a pulley or spool. The cable 250 can be wrapped around the capstan 200 one or more times around the outer surface 202 of the capstan 200. The capstan 200 may be generally cylindrical and have a first side 206 and a second side 208. The first side 206 of the capstan 200 may be considered the top side, proximal side, first end, top end, or proximal end. The second side 208 of the capstan 200 may be considered a bottom side, distal side, second end, bottom end, or distal end.

The cable 250 may extend from the capstan 200 to the pulley 260, which may be considered a redirect pulley. The cable 250 may then extend from the pulley 260 and connect to an elongate shaft or wrist or any other component of the medical instrument.

The capstan 200 may have a center hole 204 that can be supported by or mounted on a rod 210 (which can also be called a shaft, pole, or elongate portion) that may extend at least partially through the capstan 200. In some embodiments, the rod 210 can extend from a first side 206 of the capstan 200 to a second side 208 of the capstan 200. The rod 210 may be positioned along a rotational axis 212 of the capstan 200. The rotational axis 212 can also be considered a longitudinal axis.

The capstan 200 may rotate about the rotational axis 212. The capstan 200 can rotate about the rod 210 positioned along the rotational axis 212 of the capstan 200. As the capstan 200 rotates, the cable 250 wraps on or off about the outer surface 202 of the capstan 200. The cable 250 then extends to be received in the groove or redirect surface 262 of the pulley 260. The redirect surface 262 of the pulley 260 can be rotating, such that the redirect surface 262 moves or rotates as the pulley 260 rotates, such as rotating with movement of the cable 250 received therein. The redirect surface 262 can also be static, such that the redirect surface 262 and the pulley 260 do not move or rotate as the cable 250 moves along the redirect surface 262. Although the pulley 260 and redirect surface 262 are illustrated as circular, the pulley 260 or the redirect surface 262 can have other shapes. For example, the redirect surface 262 may form a u-shape or another curved surface that receives the cable 250 and changes the direction of the cable 250. The fleet angle ("α") is the angle at which the cable 250 extends from the capstan 200 to the pulley 260. The fleet angle α can be measured from a centerline or normal from the outer surface 202 of capstan 200 as shown. The fleet angle α can change due to the cable 250 wrapping on and off the capstan 200. The position of the pulley 260 can be stationary relative to the position of the capstan 200. As the capstan 200 rotates, the cable 250 can unwrap off or wrap around the outer surface 202 of the capstan 200 at different points along the length of the capstan 200, which can change the fleet angle α of the cable 250 between the capstan 200 and the pulley 260. The change in fleet angle α can change the length of the cable 250 and change tension in the cable 250. Therefore, controlling the fleet angle α to minimize the change in fleet angle α can be desirable to control tension in the system. While the change in fleet angle α can be minimized by increasing the distance between the capstan 200 and the pulley 260, this can cause complexity in arranging the various components in the instrument and can also cause an undesirable increase in size of the instrument. Additionally, maximizing the distance of the cable 250 between the capstan 200 and the pulley 260 can change tension in the system. While in several embodiments, the fleet angle is described as being minimized, it several embodiments, it can be desirable to control the or maintain the fleet angle at a constant desired angle. It can also be desirable to control or change the fleet angle at any desired angle, including maximizing or increasing the fleet angle such as to compensate for another function in the system. In some aspects, it can also be desirable to intentionally vary the fleet angle in a controlled manner.

Therefore, to control the fleet angle α, the capstan 200 can also translate relative to the rod 210, along the length of the rod 210. The capstan 200 can translate relative to the pulley along the rotational axis 212 of the capstan 200. The capstan 200 can simultaneously translate linearly along the rotational axis 212 and rotate about the rotational axis 212. This axial motion of the capstan 200 can minimize the change of fleet angle α, conserve or minimize space within the medical instrument, and gives full control over the cable 250 path length.

Figure 22B:
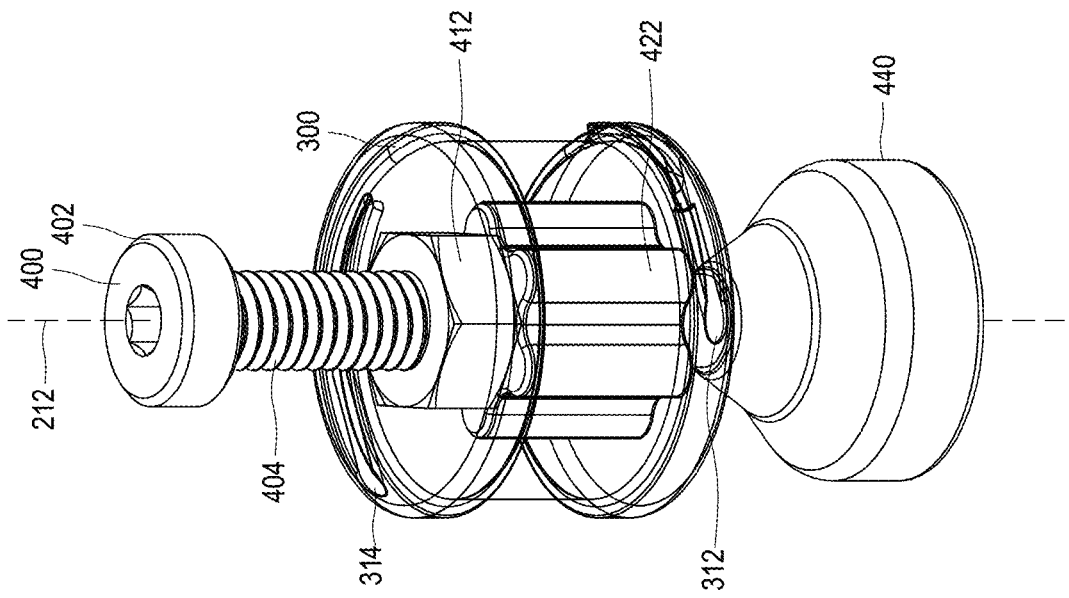
FIG. 22B illustrates the capstan of FIG. 22A with the outer surface transparent.
Figure 22A:
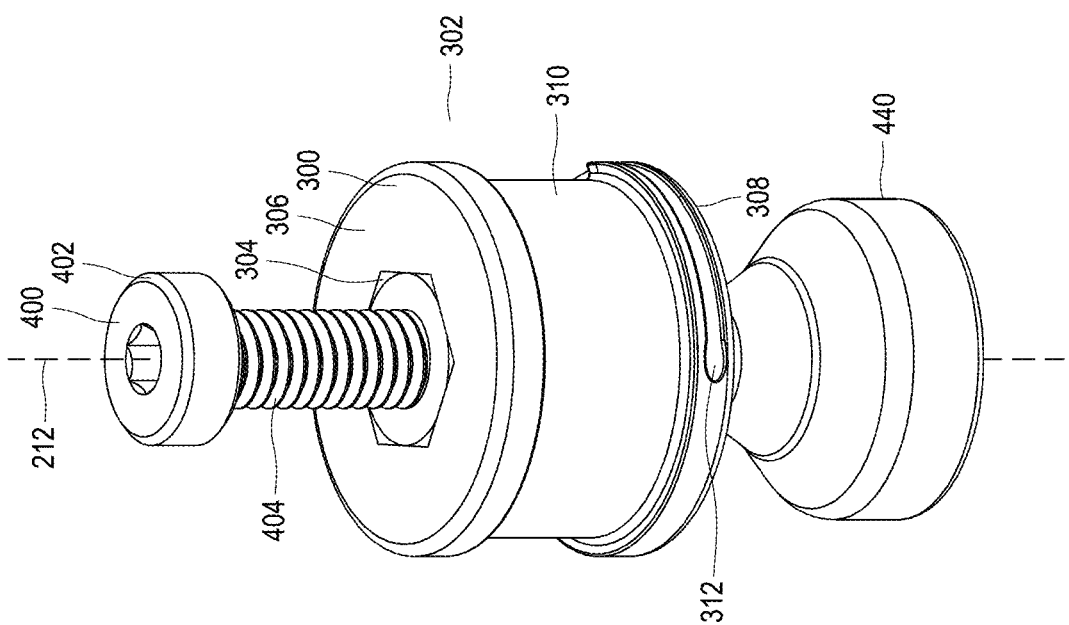
FIG. 22A illustrates a capstan connected to a drive input and a screw.

FIG. 22A illustrates a capstan 300 connected to a drive input 440 and a supporting rod 400. The capstan 300 may be generally cylindrical and have a first end 306 and a second end 308. The capstan 300 can include a groove 302 with an outer surface 310. A cable can be wrapped around the capstan 300 one or more times around the outer surface 310 of the capstan 300. The outer surface 310 can be generally smooth to allow the cable to wrap around the outer surface 310. The first and second ends 306, 308 of the outer surface 310 can be raised relative to the middle portion of the outer surface 310 to retain the cable on the capstan 300 and prevent the cable 250 from sliding or slipping off the ends of the outer surface 310. In some examples, the outer surface 310 can be considered a single large groove that is capable of receiving a cable wrapped around the outer surface 310 several times. The capstan 300 can include an anchor groove 312 to receive and secure one end of the cable. The anchor groove 312 can be positioned on the second side 308 of the capstan 300. In some examples, an anchor groove 312 can be positioned alternatively or additionally on the first side 306 of the capstan 300. As shown in FIG. 22B, the capstan 300 includes a first anchor groove 314 on the first side 306 and a second anchor groove 312 on the second side 308. This can allow a cable to be secured to the capstan 300 at one or more locations.

The drive input 440 can extend along the rotational axis 212 of the capstan 200. The drive input 440 is coupled to at least one side 308 of the capstan 200. The drive input 440 can actuate rotational motion of the capstan 300. The capstan 300 on the second side 308 can have a hole to receive and engage with the drive input 440.

The capstan 300 can also include a supporting rod 400 extending along the rotational axis 212 of the capstan 300. The supporting rod 400 can extend along the rotational axis 212 and partially through the capstan 300. The supporting rod 400 actuates axial motion of the capstan 300 as the capstan 300 rotates. The supporting rod 400 can include a top portion 402 and a bottom portion 404. The bottom portion 404 can be threaded. The supporting rod 400 can include a thread 404 coupled to the opposite side 306 of the capstan 300. The supporting rod 400 can also be considered a screw or a threaded portion itself or have a threaded portion. The capstan 300 can have a center hole 304 on the first side 306 to receive at least a portion of the bottom portion 404 of the supporting rod 400. In some aspects, the center hole 304 can extend from the first end 306 to the second end 308 of the capstan 300. In some aspects, the center hole 304 can extend from the first side 306 and partially into the capstan 300. In some aspects, the second side 308 can have a center hole (not shown) that can extend from the second side 308 and partially into the capstan 300 to receive and engage with the drive input 440.

Although the supporting rod 400 is shown coupled to the first side 306 and the drive input 440 is shown coupled to the second side 308 in FIG. 22A, the support rod 400 can also be coupled to the second side 308 and the drive input 440 can be coupled to the first side 306. In some aspects, the supporting rod 400 can extend at least from the first side 306 of the capstan to the second side 308 of the capstan 300. The supporting rod 400 can extend partially at least from the first side 306 of the capstan and partially into the capstan 300.

As described, the capstan 300 can be rotated by the drive input 440. Rotation of the capstan 300 by the drive input 440 can also cause rotation of the capstan 300 with respect to the threaded portion 404 of the supporting rod 400. As the capstan 300 rotates relative to the threaded portion 404, the capstan 300 will axially translate the capstan 300 along the threaded portion 404.

FIG. 22B illustrates the capstan 300 of FIG. 22A with the outer surface of the capstan 300 transparent to illustrate the inner components. The capstan 300 can have a spline 422 and a nut 412 positioned internally within the capstan 300. In some aspects, the spline 422 or the nut 412 can be integral with the capstan 300 and be considered part of the capstan 300. In some aspects, the spline 422 or the nut 412 can be separate components from the capstan 300, but received within a corresponding hole or groove 304 of the capstan 300. The spline 422 can extend along the rotational axis 212 of the capstan 300. The spline 422 can be coupled to at least the second side 308 of the capstan 300. In some examples, the spline 422 can be alternatively or additionally coupled to the first side 306 of the capstan 300. The spline 422 can actuate rotational motion of the capstan 300. The spline 422 can be configured to engage with or receive at least a portion of the drive input 440. The nut 412 can be configured to engage with and receive at least a part of the threaded portion 404. FIG. 22B illustrates the spline 422 positioned within the hole 304 that can be shaped to receive the spline 422. The spline 422 can engage with or connect to the drive input 440, such that rotation of the drive input 440 will rotate the spline 422, which will in turn rotate the capstan 300.

The capstan 300 can be configured to move longitudinally along the rotational axis 212 of the capstan 300. As the capstan 300 is rotated, actuated by the drive input 440 and spline 422, the capstan 300 can translate axially relative to the supporting rod 400 received in the nut 412. As the capstan 300 is rotated by the drive input 440, the nut 412 positioned within the capstan 300 will rotate relative to the threaded portion 404 and thus will axially translate relative to the threaded portion 404 based on the pitch of the threaded portion 404.

Although the bottom portion 404 of the supporting rod 400 is shown as threaded to be received within the female threads of the nut 412, in a modified arrangement the threaded arrangement can be reversed. For example, in modified arrangement, the capstan 300 can include an attached or integrated threaded rod which is received within corresponding female threads in a surrounding housing (external from the capstan). As with the illustrated embodiment, rotation of the capstan would cause axial movement as coupled or integrated threaded rod of the capstan rotates within the female threads of the surrounding housing.

Although the bottom portion 404 of the supporting rod 400 is shown as threaded, the supporting rod 210 can also be smooth and allow the capstan 200 to slide axially relative to the rod 210. As the drive input 440 actuates rotation of the capstan 300, the cable 250 can wrap on and off the capstan 300 and the capstan 300 can axially slide along the rod 210. The axial motion of the capstan 300 can be actuated by a screw (not shown) positioned off-axis from the capstan 300.

Figure 23:
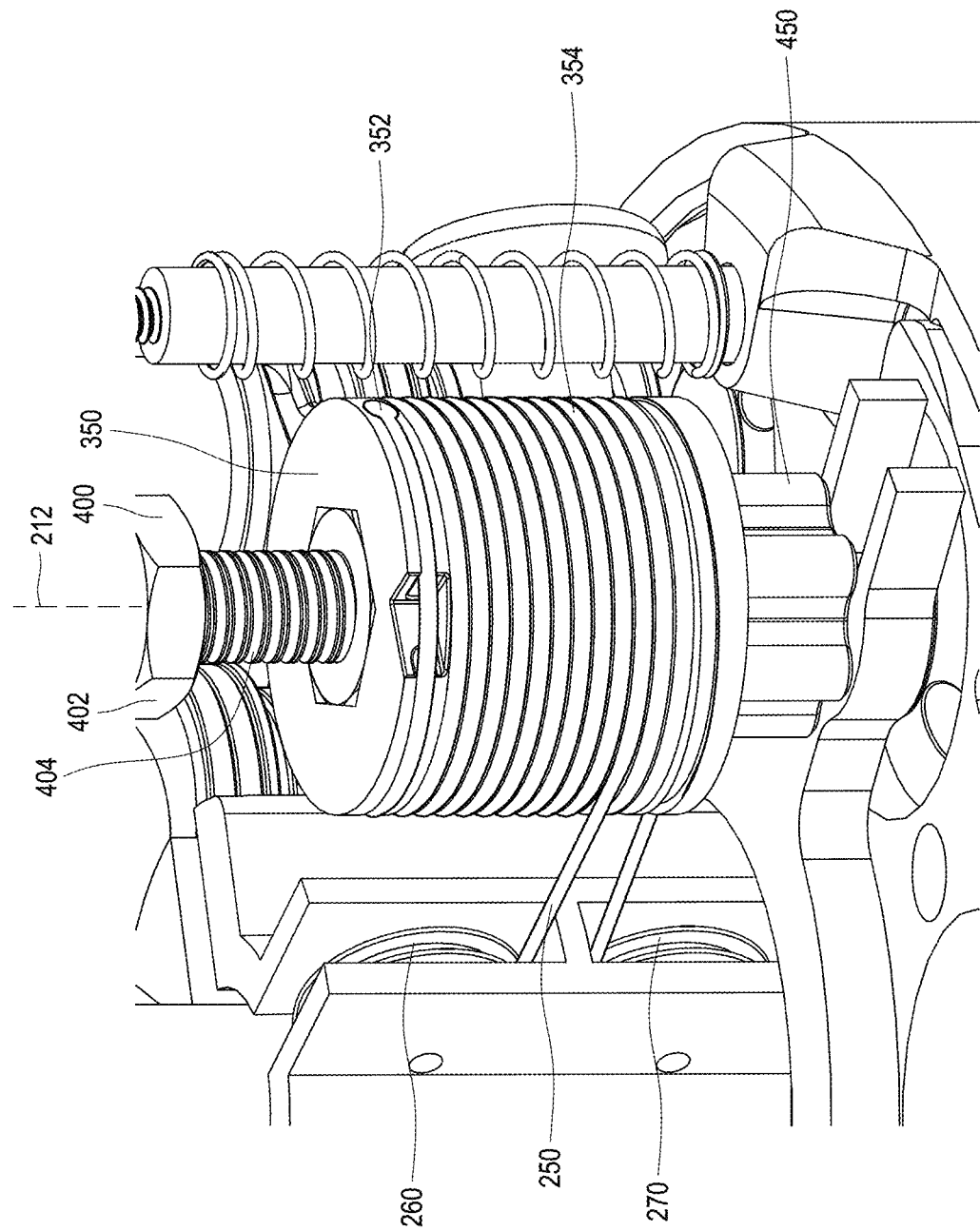
FIG. 23 illustrates a cable connected to a capstan and a pulley in a handle of a medical instrument.

FIG. 23 illustrates a cable 250 connected to a capstan 350 and a pulley 260 in a handle of a medical instrument. The capstan 350 may be similar to the capstan 300 as described in FIGS. 22A and 22B. The capstan 350 can connect to the supporting rod or screw 400 similar to FIGS. 22A and 22B.

The spline 450 may extend from the capstan 350. In some aspects, the spline 450 may be considered separate from the capstan 350 and can be configured to attach to the capstan 350. The spline 450 may be received within a hole or groove (not shown) of the capstan 350. The spline 450 may be positioned internally within this hole or groove of the capstan 350 and also extend externally from the capstan 350. In some aspects, the spline 450 may be integral with the capstan 350 such that it is considered part of the capstan 300. The spline 450 may engage with or be coupled to a drive input. In some aspects, the spline 450 may extend from the capstan 350 and be received within a groove or recess of a separate piece (not shown) to receive the spline 450. The separate piece may then connect to and be driven by a drive input.

The cable 250 can wrap around the outer surface 354 of the capstan 350. One end of the cable 250 can extend from the outer surface 354 of the capstan 350 to a first pulley 260 while the other end of the cable 250 can extend from the outer surface 354 of the capstan 350 to a second pulley 270. The first and second pulleys 260, 270 can also be positioned in the handle of the medical instrument. The capstan 350 can include an anchor groove 352 to receive and secure one end of the cable 250. This can allow one end of the cable 250 to be secured to the capstan 300.

The capstan 350 can have a helical groove 352 on an outer surface 354 of the capstan 350. The helical groove 352 can receive the cable 250 as the cable 250 is wrapped around the capstan 350. The helical groove 352 can advantageously help with the cable life and assembly.

The pitch of the threaded portion 404 of the supporting rod or screw 400 matches a pitch of a helical groove 352 of the capstan 350. The capstan 350 is configured to move longitudinally along the rotational axis 212 of the capstan 350 as the capstan 350 is rotated (as actuated by the spline 450). The pitch of the threaded portion 404 of the screw 400 matching the pitch of the helical groove 352 of the capstan 350 allows the capstan 350 to rotate about the rotational axis 212 at the same rate the capstan 350 linearly translates along the rotational axis 212. The coordinated rotational and translational motion of the capstan 350 can control the fleet angle of the cable 250 between the capstan 350 and the pulley 260. Rotational motion of the capstan 350 can cause the capstan 350 to axially move on the screw 400 as the capstan 350 is rotated.

Figure 24:
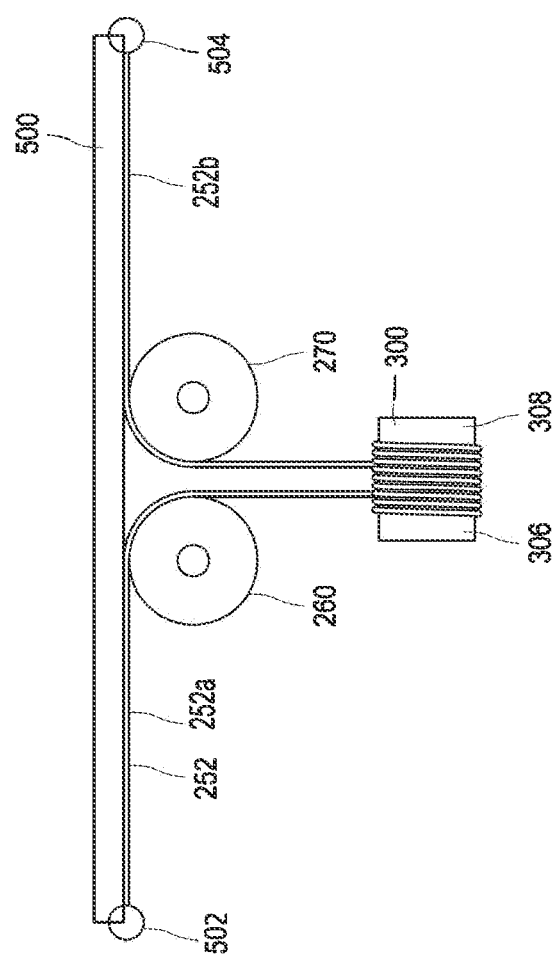
FIG. 24 illustrates a cable connected to a capstan and an elongated shaft of a medical instrument.

FIG. 24 illustrates one or more cables 252 connected to a capstan 300 and an elongated shaft 500 of a medical instrument. The elongate shaft 500 can be operatively coupled to the capstan 300 and the first pulley 260 and a second pulley 270. The elongate shaft 500 can include a proximal portion 502 and a distal portion 504. The elongate shaft 500 can include an end effector (not shown), which may be connected to the distal portion of the elongate shaft 500. The rotation of the capstan 300 and corresponding shortening or lengthening of the one or more cables 252 can actuate the end effector. The rotation of the capstan 300 and corresponding shortening or lengthening of the one or more cables can also actuate linear translation of the elongate shaft 500.

A first end of the one or more cables 252 can terminate at the proximal portion 502 of the shaft 500 and a second end of the one or more cables 252 can terminate at the distal portion 504 of the shaft 500. In some embodiments, the one or more cables 252 can be a single cable that terminates at the proximal portion 502 of the shaft 500 and connects to and wraps around the capstan 300 and also terminates at the distal portion 504 of the shaft 500. The one or more cables 252 can connect on a distal side 308 of the capstan 300 and can connect on a proximal side 306 of the capstan 300.

The one or more cables 252 can also be connected to the first pulley 260 and the second pulley 270. The one or more cables 252 can wrap around the proximal side 306 of the capstan 300, about the first pulley 260, and extend to the proximal portion 502 of the elongate shaft 500. In some embodiments, the one or more cables 252 can wrap around the proximal side 306 of the capstan 300 and extend from the middle portion of the capstan 300 to the first pulley, as shown in FIG. 24. In other embodiments, the one or more cables 252 can wrap around the proximal side 306 of the capstan 300 and extend from the proximal side 306 of the capstan 300 to the first pulley 260. The one or more cables 252 can also wrap around the distal side 308 of the capstan 300, about the second pulley 270, and extend to the distal portion 504 of the elongate shaft 500. In some embodiments, the one or more cables 252 can wrap around the distal side 308 of the capstan 300 and extend from the middle portion of the capstan 300 to the second pulley 270, as shown in FIG. 24. In other embodiments, the one or more cables 252 can wrap around the distal side 308 of the capstan 300 and extend from the distal side 308 of the capstan 300 to the second pulley 270.

Rotation of the capstan 300 can cause shortening of the one or more cable 250 at the distal side 308 of the capstan and a corresponding lengthening of the cable at the proximal side 306 of the capstan 300. Rotation of the capstan 300 causes linear translation of the shaft 500 relative to the position of the capstan 300 of the medical instrument or device.

The one or more cables 252 can wrap on and off the capstan 300 actuated by rotation of the capstan 300. When the one or more cables 252 is wound about the capstan 300 at the distal side 308 of the capstan 300 during linear translation of the shaft 500 in a first direction. The first direction may be a linear direction parallel to the length of the elongate shaft 500. When the one or more cables 252 is unwound from the capstan 300 at the proximal side 306 of the capstan 350 during linear translation of the shaft 500 in a second direction. The second direction can be a linear direction parallel to the length of the elongate shaft and can be opposite from the first direction.

In some embodiments, the one or more cables 252 can include at least two cables. One end of the first cable 252a can attach and terminate to the proximal portion 502 of the shaft 500. The first cable 252a can wrap around a first end 306 of the capstan 300. The second end of the first cable 252a can terminate on the first side 306 of the capstan 300. The second cable 252b of the at least two cables can attach to and terminate on the distal portion 504 of the elongate shaft 500. The second cable 252b can wrap around the second end 308 of the capstan 300.

The first cable 252a can be connected to the first pulley 260 and the second cable 252b can be connected to the second pulley 270. The first cable 252a can extend from the proximal side 306 of the capstan 300, about the first pulley 260, and extend to the proximal portion 502 of the elongate shaft 500. The second cable 252b can also extend from the distal side 308 of the capstan 300, about the second pulley 270, and extend to the distal portion 504 of the elongate shaft 500.

The second end of the second cable 252b can terminate on the second end 308 of the capstan 300. The capstan 300 can be rotated in a first rotational direction to cause winding of the first cable 252a around the capstan 300 and a corresponding unwinding of the second cable 252b from the capstan 300. The first rotational direction can be a rotational direction, such as clockwise. The capstan 300 can be rotated in a second rotational direction to cause unwinding of the first cable 252a around the capstan 300 and a corresponding winding of the second cable 252b from the capstan 300. The second rotational direction can be a rotational direction opposite from the first rotational direction, such as counterclockwise. Winding of the first cable 252a around the capstan 300 and unwinding of the second cable 252b from the capstan 300 can cause linear translation of the shaft 500 in a first linear direction. Unwinding of the first cable 252a around the capstan 300 and winding of the second cable 252b from the capstan 300 can cause linear translation of the shaft in a second linear direction.

Rotating the capstan 300 in a first rotational direction about a rotational axis can impart movement to a pull wire 252 extending around a pulley 260 in a first direction. The distal end 504 of the medical device can be moved in a first direction via movement of the pull wire 252. In some embodiments, the distal end 504 can be actuated to move the shaft 500 of the medical device in a first linear direction via movement of the pull wire 252. In some embodiments, the distal end 504 can be deflected in any direction.

The capstan 300 can be translated along the rotational axis in concert with rotating the capstan 300 in the first rotational direction to control a fleet angle of the pull wire 252 between the capstan 300 and the pulley 260. The pull wire 252 can wrap on the capstan 300 as the capstan 300 rotates in a first rotational direction. The pull wire 252 can wrap off the capstan 300 as the capstan 300 rotates in a second rotational direction. The fleet angle can be the angle the pull wire 252 wraps on and off the capstan 300. The change in the fleet angle can be maintained within an angle range between 0-45 degrees, such as between 0-1 degrees, 0-2 degrees, 0-5 degrees, 0-10 degrees, 0-15 degrees, 0-20 degrees, 0-25 degrees, 0-30 degrees, 0-40 degrees, 5-10 degrees, or 5-15. Optionally, the second pulley 270 can similarly actuate movement of the same pull wire or a different pull wire to connect to and actuate the proximal portion 502 of the elongate shaft 500.

Figure 25:
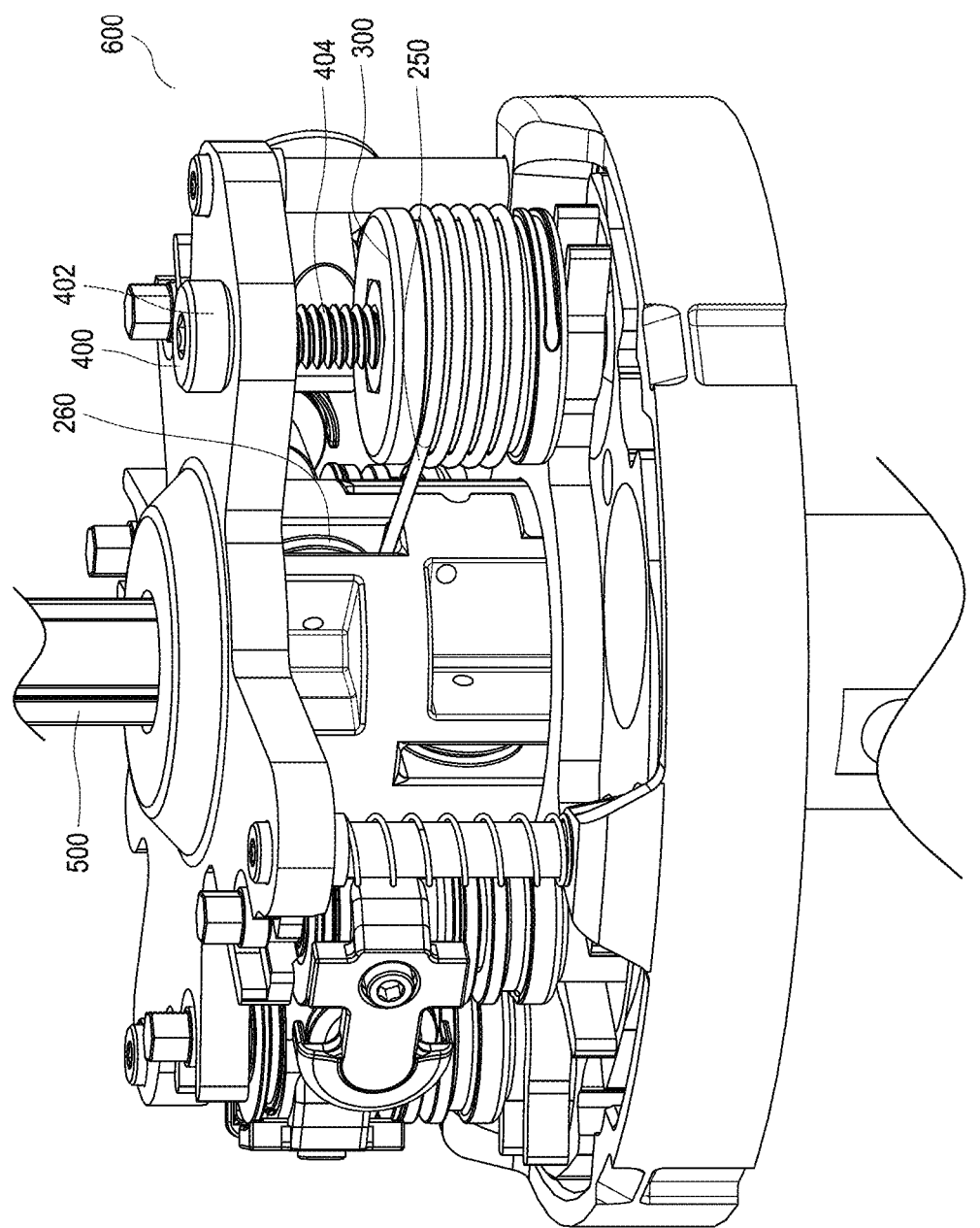
FIG. 25 illustrates a cable connected to a capstan and pulley within a handle.
Figure 26:
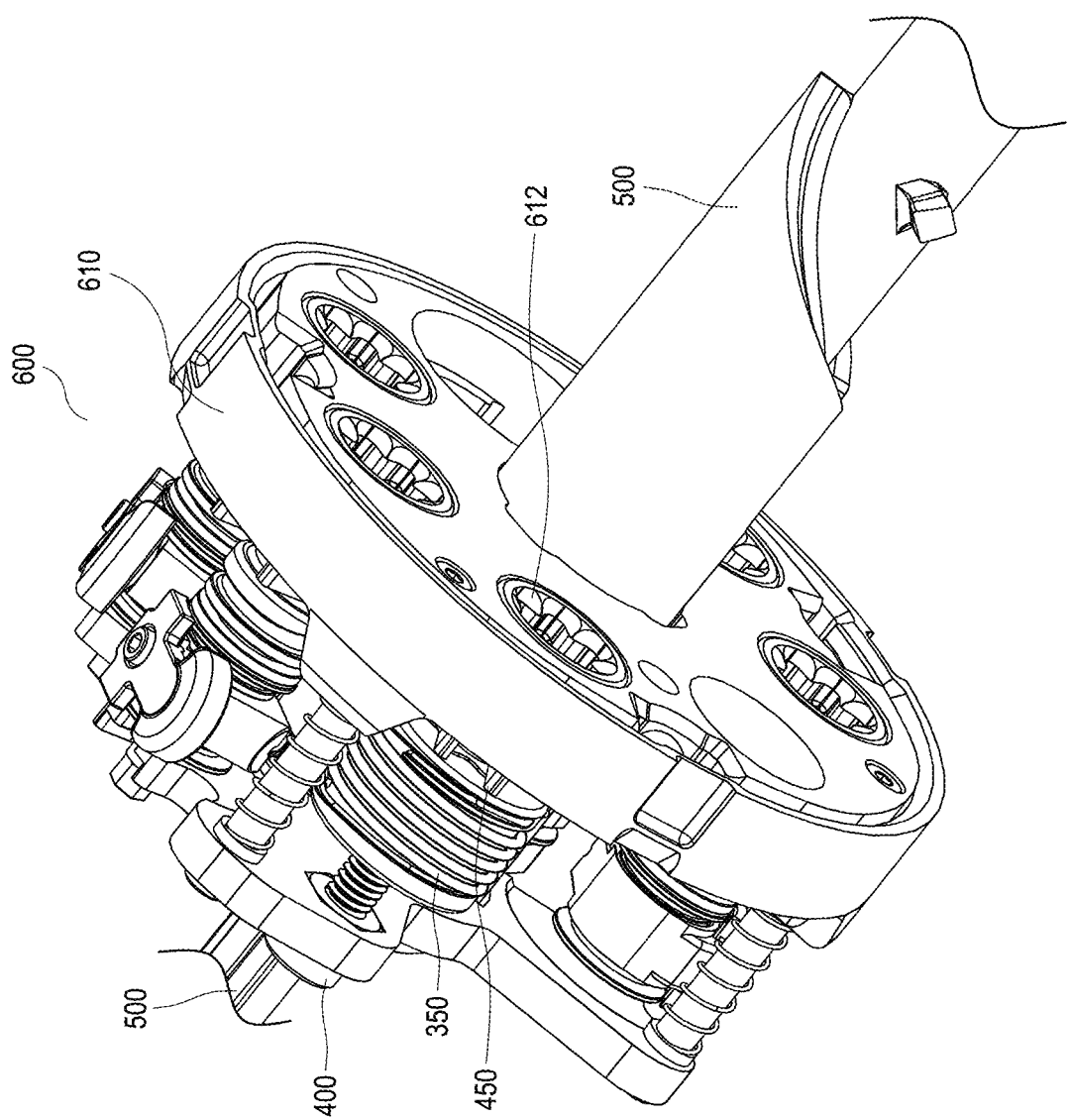
FIG. 26 illustrates a cable connected to a capstan within a handle with one or more drive inputs.

FIG. 25 illustrates a cable 250 connected to the capstan 300 and connected to a pulley 260 within the handle 600 of a medical device. The cable 250 can then extend from the pulley 260 to the elongate shaft 500. FIG. 26 illustrates a cable 250 connected to the capstan 350 within a handle 600 with one or more drive inputs 612. The elongate shaft 500 can be coupled to a handle 600.

Rotation of the capstan 350 can cause linear translation of the shaft 500 relative to the handle 600 of the medical device. Rotational motion of the capstan 350 can cause the capstan 350 to axially move on a screw 400 fixed to the handle 600 as the capstan 350 is rotated. Rotational motion of the capstan 350 can cause the capstan 350 to axially move on the screw 400 fixed to the handle 600 as the capstan 350 is rotated. A cable 250 can be wrapped around the capstan 350. The cable 250 can extend from the capstan 350 to the pulley 260 at a fleet angle.

The medical instrument can be attached to an instrument drive mechanism or instrument driver that is positioned on the end of a robotic arm or other instrument positioning device. The instrument drive mechanism can include one or more robotic drive outputs that engage one or more robotic drive inputs or drive shafts 612 to robotically control the medical instrument. In some aspects, the medical instrument can include the instrument handle 600, which can include one or more rotational drive inputs or drive shafts 612. The one or more pullwires 250 may be actuated to articulate an elongated shaft 500 or the wrist of the tool. The one or more pullwires 250 may also be actuated to translate an elongate shaft 500 relative to the instrument handle 600. The drive inputs 612 of the handle 600 can be driven by an instrument driver with one or more drive outputs, similar to the instrument driver shown in FIG. 17. The drive inputs 612 can receive the drive outputs (similar to the drive outputs 81 as shown in FIG. 17).

The spline 450 can be coupled to and driven by a drive input 612 of the handle 600. The capstan 350 can be rotated by the spline 450, as described herein. The drive inputs 612 can then be rotated by the drive outputs of the instrument driver to actuate rotational movement of the capstan 350 through the connected spline 450. The other drive inputs 612 may be used for other types of articulation and actuation. The handle 600 can include other spools or pulleys and pull wires for other types of articulation or actuation.

The spline 450 can be connected to the capstan 350 as described herein. The instrument driver can be configured to control the fleet angle of the cable 252 by urging translation of the capstan 350 as the capstan 350 rotates. The instrument driver can control the fleet angle by moving the capstan 350 longitudinally along a rotational axis of the capstan 350 in concert with rotation of the capstan 350 about the rotational axis of the capstan 350. The capstan 350 can be mounted on the screw 400 and configured to move the capstan 350 axially relative to the screw 400 as the capstan 350 rotates. Axial movement of the capstan 350 can be configured to control the fleet angle of the first cable 250 wrapping on or off the capstan 350.

3. Implementing Systems and Terminology

Implementations disclosed herein provide systems, methods and apparatus related to capstans for robotically controllable medical instruments.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The specific computer-implemented functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical device comprising:
a redirect surface;
a capstan supported for rotation about a rotational axis and translation along the rotational axis;
a cable wrapped around the capstan and extending from the capstan to the redirect surface;
a shaft comprising a proximal portion and a distal portion, wherein a first end of the cable terminates at the proximal portion of the shaft and a second end of the cable terminates at the distal portion of the shaft; and
a handle coupled to the shaft,
wherein rotation of the capstan causes linear translation of the shaft relative to the handle of the medical device and the capstan is configured to translate relative to the redirect surface along the rotational axis as the capstan rotates about the rotational axis.

2. The medical device of claim 1, further comprising a supporting rod extending along the rotational axis of the capstan, wherein the supporting rod comprises a thread coupled to a first side of the capstan, wherein the supporting rod actuates axial motion of the capstan as the capstan rotates.

3. The medical device of claim 1, further comprising a threaded portion extending along the rotational axis and partially through the capstan, wherein rotation of the capstan with respect to the threaded portion causes axial translation of the capstan along the threaded portion.

4. The medical device of claim 3, further comprising a helical groove of an outer surface of the capstan, the helical groove configured to receive the cable as the cable is wrapped around the capstan, wherein a pitch of the threaded portion matches a pitch of a helical groove.

5. The medical device of claim 1, further comprising a spline extending along the rotational axis of the capstan, wherein the spline is coupled to at least a second side of the capstan, wherein the spline actuates rotational motion of the capstan.

6. The medical device of claim 1, further comprising a support rod extending along the rotational axis of the capstan, the supporting rod extending at least from a first side of the capstan to a second side of the capstan, wherein the capstan is configured to slide axially relative to the supporting rod.

7. The medical device of claim 1, wherein the capstan is configured to move longitudinally along the rotational axis of the capstan to control a fleet angle between the capstan and the redirect surface.

8. The medical device of claim 1,
wherein:
the cable connects on a distal side of the capstan and connects on a proximal side of the capstan,
rotation of the capstan causes shortening of the cable at the distal side of the capstan and a corresponding lengthening of the cable at the proximal side of the capstan,
the cable is wound about the capstan at the distal side of the capstan during linear translation of the shaft relative to the handle in a first direction, and
the cable is unwound from the capstan at the proximal side of the capstan during linear translation of the shaft relative to the handle in a second direction, wherein the second direction is opposite from the first direction.

9. The medical device of claim 1, wherein the capstan is rotated by a spline, wherein the spline is coupled to and driven by a drive input of the handle.

10. The medical device of claim 1, wherein rotational motion of the capstan causes the capstan to axially move on a screw fixed to the handle as the capstan is rotated.

11. The medical device of claim 1, further comprising an end effector connected to the distal portion of the shaft.

12. The medical device of claim 1, wherein the redirect surface is a pulley.

13. A robotic medical system comprising:
a pulley;
a capstan;
a cable wrapped around the capstan, the cable extending from the capstan to the pulley at a fleet angle;
a shaft comprising a proximal portion and a distal portion, wherein a first end of the cable terminates at the proximal portion of the shaft and a second end of the cable terminates at the distal portion of the shaft; and
an instrument driver configured to control the fleet angle of the cable by urging translation of the capstan as the capstan rotates, wherein rotation of the capstan causes linear translation of the shaft.

14. The robotic medical system of claim 13, wherein the instrument driver controls the fleet angle by moving the capstan longitudinally along a rotational axis of the capstan in concert with rotation of the capstan about the rotational axis of the capstan.

15. The robotic medical system of claim 13, wherein the capstan is mounted on a screw configured to move the capstan axially relative to the screw as the capstan rotates, wherein axial movement of the capstan is configured to control the fleet angle of the cable wrapping on or off the capstan.

16. The robotic medical system of claim 15, wherein a change in the fleet angle is maintained within an angle range between 0 degrees to 10 degrees.

17. The robotic medical system of claim 13, wherein:
the cable connects on a distal side of the capstan and connects on a proximal side of the capstan,
rotation of the capstan causes shortening of the cable at the distal side of the capstan and a corresponding lengthening of the cable at the proximal side of the capstan,
the cable is wound about the capstan at the distal side of the capstan during linear translation of the shaft in a first direction, and
the cable is unwound from the capstan at the proximal side of the capstan during linear translation of the shaft in a second direction, wherein the second direction is opposite from the first direction.

18. A method of operating a medical device comprising:
rotating a capstan in a first rotational direction about a rotational axis to impart movement to a pull wire extending around a pulley in a first direction;
moving a distal end of the medical device via movement of the pull wire;
translating the capstan along the rotational axis in concert with rotating the capstan in the first rotational direction to control a fleet angle of the pull wire between the capstan and the pulley; and
moving a shaft of the medical device in a first linear direction via movement of the pull wire.

19. The method of claim 18, wherein a change in the fleet angle is maintained within an angle range between 0 degrees to 10 degrees.

20. The method of claim 18, further comprising: wrapping the pull wire on the capstan as the capstan rotates in a first rotational direction; and unwrapping the pull wire off the capstan as the capstan rotates in a second rotational direction.

21. The method of claim 18, further comprising:
winding the pull wire about the capstan at a distal side of the capstan during linear translation of the shaft in a first direction.

22. The method of claim 21, further comprising:
unwinding the pull wire from the capstan at a proximal side of the capstan during linear translation of the shaft in a second direction, wherein the second direction is opposite from the first direction.

23. A medical device comprising:
a shaft comprising a proximal portion and a distal portion;
a redirect surface;
a capstan supported for rotation about a rotational axis and translation along the rotational axis;
a cable wrapped around the capstan and extending from the capstan to the redirect surface; and
a second cable wrapped around the capstan, wherein:
a first end of the cable terminates at the proximal portion of the shaft and a second end of the cable terminates at a first side of the capstan,
a first end of the second cable terminates at the distal portion of the shaft and a second end of the second cable terminates at a second side of the capstan,
rotation of the capstan in a first rotational direction causes winding of the cable around the capstan and a corresponding unwinding of the second cable from the capstan,
rotation of the capstan in a second rotational direction causes unwinding of the cable around the capstan and a corresponding winding of the second cable from the capstan,
winding of the cable around the capstan and unwinding of the second cable from the capstan causes linear translation of the shaft in a first linear direction,
unwinding of the cable around the capstan and winding of the second cable from the capstan causes linear translation of the shaft in a second linear direction, and
the capstan is configured to translate relative to the redirect surface along the rotational axis as the capstan rotates about the rotational axis.

* * * * *